US012797567B2

(12) United States Patent
Lui et al.

(10) Patent No.: US 12,797,567 B2
(45) Date of Patent: Nov. 17, 2026

(54) CONTROL OF COMPONENTS OF A BREATHING ASSISTANCE APPARATUS

(71) Applicant: Fisher & Paykel Healthcare Limited, Auckland (NZ)

(72) Inventors: Minghon Carlton Lui, Auckland (NZ); Jack Che-Wei Hsu, Auckland (NZ); Luca Ortali, Auckland (NZ); Jae Chul Han, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 433 days.

(21) Appl. No.: 18/560,664

(22) PCT Filed: May 26, 2022

(86) PCT No.: PCT/IB2022/054939

§ 371 (c)(1),
(2) Date: Nov. 13, 2023

(87) PCT Pub. No.: WO2022/249117

PCT Pub. Date: Dec. 1, 2022

(65) Prior Publication Data

US 2024/0252772 A1 Aug. 1, 2024

Related U.S. Application Data

(60) Provisional application No. 63/193,551, filed on May 26, 2021.

(51) Int. Cl.

| | |
|---|---|
| ***A61M 16/00*** | (2006.01) |
| ***A61M 16/10*** | (2006.01) |
| ***A61M 16/16*** | (2006.01) |

(52) U.S. Cl.

CPC ...... *A61M 16/024* (2017.08); *A61M 16/0066* (2013.01); *A61M 16/1095* (2014.02); (Continued)

(58) Field of Classification Search

CPC .... A61H 16/0875; A61H 16/16; A61H 16/18; A61H 16/1085; A61H 16/109; A61H 16/1095

See application file for complete search history.

(56) References Cited

U.S. PATENT DOCUMENTS

| | | |
|---|---|---|
| 3,893,458 A | 7/1975 | Fletcher et al. |
| 4,110,419 A | 8/1978 | Miller |

(Continued)

FOREIGN PATENT DOCUMENTS

| | | |
|---|---|---|
| AU | 2006250091 | 7/2009 |
| CN | 1314192 | 11/2004 |

(Continued)

OTHER PUBLICATIONS

Humidaire2 2i User Manual (2001 on sale, User Manual dated 2003); in 26 pages.

(Continued)

*Primary Examiner* — Paige Kathleen Bugg
*Assistant Examiner* — Jaeick Jang
(74) *Attorney, Agent, or Firm* — Knobbe, Martens, Olson & Bear, LLP

(57) ABSTRACT

Disclosed is an apparatus, where a controller of the apparatus is configured to control at least one heater according to at least a first control scheme when powered by a battery and a second control scheme when powered by a mains power supply.

18 Claims, 13 Drawing Sheets

(52) U.S. Cl.
CPC .......... *A61M 16/16* (2013.01); *A61M 16/109* (2014.02); *A61M 2205/8206* (2013.01)

(56) References Cited

U.S. PATENT DOCUMENTS

| | | | |
|---|---|---|---|
| 4,391,271 | A | 7/1983 | Blanco |
| 4,722,334 | A | 2/1988 | Blackmer et al. |
| 4,955,372 | A | 9/1990 | Blackmer et al. |
| 5,503,146 | A | 4/1996 | Froehlich et al. |
| 5,537,966 | A | 7/1996 | McPhee et al. |
| 5,551,419 | A | 9/1996 | Froehlich |
| 5,558,084 | A | 9/1996 | Daniell et al. |
| 5,696,686 | A | 12/1997 | Sanka et al. |
| 5,862,802 | A | 1/1999 | Bird |
| 6,240,921 | B1 | 6/2001 | Brydon et al. |
| 6,283,132 | B1 | 9/2001 | Stephens et al. |
| 6,367,472 | B1 | 4/2002 | Koch |
| 6,435,180 | B1 | 8/2002 | Hewson et al. |
| 6,523,538 | B1 | 2/2003 | Wikefeldt |
| 6,895,803 | B2 | 5/2005 | Seakins et al. |
| 7,007,692 | B2 | 3/2006 | Aylsworth et al. |
| 7,111,624 | B2 | 9/2006 | Thurdor et al. |
| 7,140,367 | B2 | 11/2006 | White et al. |
| 7,306,205 | B2 | 12/2007 | Huddart et al. |
| 7,343,917 | B2 | 3/2008 | Jones |
| 7,493,902 | B2 | 2/2009 | White et al. |
| 7,802,569 | B2 | 9/2010 | Yeates et al. |
| 7,882,834 | B2 | 2/2011 | Gradon et al. |
| 8,015,971 | B2 | 9/2011 | Kwok |
| 8,020,558 | B2 | 9/2011 | Christopher et al. |
| 8,453,641 | B2 | 6/2013 | Payton et al. |
| 8,550,072 | B2 | 10/2013 | Thurdor et al. |
| 8,733,353 | B2 | 5/2014 | Kramer et al. |
| 8,741,220 | B2 | 6/2014 | O'Donnell et al. |
| 8,844,522 | B2 | 9/2014 | Huby et al. |
| 8,893,715 | B2 | 11/2014 | Payton et al. |
| 9,168,350 | B2 | 10/2015 | Payton et al. |
| 9,180,266 | B1 | 11/2015 | Sherman |
| 9,526,807 | B2 | 12/2016 | O'Donnell et al. |
| 9,839,759 | B2 | 12/2017 | Payton et al. |
| D841,148 | S | 2/2019 | Stok et al. |
| 10,350,379 | B2 | 7/2019 | Sweeney et al. |
| D865,943 | S | 11/2019 | Wilson et al. |
| D870,269 | S | 12/2019 | Klenner et al. |
| 10,512,702 | B2 | 12/2019 | O'Donnell et al. |
| 10,555,703 | B2 | 2/2020 | Stapelfeldt |
| D880,686 | S | 4/2020 | Stoks et al. |
| 10,918,821 | B2 | 2/2021 | Payton et al. |
| 11,285,290 | B2 | 3/2022 | Barker et al. |
| 11,576,990 | B2 | 2/2023 | O'Donnell et al. |
| 11,679,228 | B2 | 6/2023 | Payton et al. |
| 12,076,457 | B2 | 9/2024 | O'Donnell et al. |
| 12,194,245 | B2 | 1/2025 | Payton et al. |
| 2001/0050080 | A1 | 12/2001 | Seakins et al. |
| 2002/0124847 | A1 | 9/2002 | Smith et al. |
| 2003/0066526 | A1 | 4/2003 | Thudor |
| 2003/0094178 | A1 | 5/2003 | McAuley |
| 2003/0154977 | A1 | 8/2003 | White et al. |
| 2003/0209246 | A1 | 11/2003 | Schroeder et al. |
| 2004/0079370 | A1 | 4/2004 | Gradon et al. |
| 2004/0149284 | A1 | 8/2004 | Smith et al. |
| 2004/0221844 | A1 | 11/2004 | Hunt et al. |
| 2004/0261797 | A1 | 12/2004 | White et al. |
| 2006/0027234 | A1 | 2/2006 | Gradon et al. |
| 2007/0144514 | A1 | 6/2007 | Yeates et al. |
| 2007/0277827 | A1 | 12/2007 | Bordewick et al. |
| 2008/0028850 | A1 | 2/2008 | Payton et al. |
| 2008/0053441 | A1 | 3/2008 | Gottlib et al. |
| 2008/0072900 | A1 | 3/2008 | Kenyon et al. |
| 2008/0092898 | A1 | 4/2008 | Schneider |
| 2008/0099017 | A1 | 5/2008 | Bordewick et al. |
| 2008/0196722 | A1 | 8/2008 | Kramer et al. |
| 2008/0310994 | A1 | 12/2008 | O'Donnell et al. |
| 2009/0014012 | A1 | 1/2009 | Sanders |
| 2009/0071478 | A1 | 3/2009 | Kalfon et al. |
| 2010/0065054 | A1* | 3/2010 | Bowman .......... A61M 16/0051 128/204.21 |
| 2011/0162647 | A1 | 7/2011 | Huby et al. |
| 2012/0037156 | A9 | 2/2012 | Tatkov et al. |
| 2012/0048271 | A1 | 3/2012 | O'Donnell et al. |
| 2014/0366876 | A1 | 12/2014 | Huby et al. |
| 2015/0051449 | A1 | 2/2015 | Qiu |
| 2015/0273172 | A1 | 10/2015 | Pessala et al. |
| 2015/0343167 | A1 | 12/2015 | Rybicki |
| 2016/0029949 | A1 | 2/2016 | Landesberg et al. |
| 2018/0336711 | A1 | 11/2018 | Brogger |
| 2019/0143060 | A1 | 5/2019 | Jafari et al. |
| 2019/0150831 | A1 | 5/2019 | Payton et al. |
| 2019/0224434 | A1 | 7/2019 | Silver et al. |
| 2019/0275281 | A1 | 9/2019 | Harrington et al. |
| 2019/0336711 | A1 | 11/2019 | O'Donnell et al. |
| 2019/0344032 | A1 | 11/2019 | McCormick et al. |
| 2020/0114098 | A1* | 4/2020 | Bath ................ A61M 16/0066 |
| 2021/0016033 | A1 | 1/2021 | Boehm |
| 2021/0128864 | A1 | 5/2021 | Vicario et al. |
| 2021/0138180 | A1 | 5/2021 | Sweeney et al. |
| 2021/0205569 | A1 | 7/2021 | Kwok |
| 2022/0023571 | A1 | 1/2022 | Landis et al. |
| 2024/0108847 | A1 | 4/2024 | Payton et al. |
| 2024/0207567 | A1 | 6/2024 | Vadnerkar et al. |
| 2024/0350759 | A1 | 10/2024 | Matthews et al. |
| 2024/0358947 | A1 | 10/2024 | Barnes et al. |
| 2025/0073364 | A1 | 3/2025 | O'Donnell et al. |
| 2025/0161607 | A1 | 5/2025 | Ellingham et al. |

FOREIGN PATENT DOCUMENTS

| | | |
|---|---|---|
| EP | 2 055 336 | 5/2009 |
| EP | 2055336 A1 | 5/2009 |
| GB | 2338420 | 12/1999 |
| JP | H04-54968 | 2/1992 |
| JP | H04-352965 | 12/1992 |
| JP | H08-252314 | 10/1996 |
| JP | H08-299307 | 11/1996 |
| JP | H09-234247 | 9/1997 |
| JP | 2001-321443 | 11/2001 |
| JP | H07-204273 | 12/2001 |
| JP | 2005-201822 | 7/2005 |
| JP | 3111440 | 7/2005 |
| JP | 2020-168087 | 10/2020 |
| JP | D1671416 | 11/2020 |
| KR | 10-0359274 B1 | 1/2003 |
| WO | WO 2001/013981 | 3/2001 |
| WO | WO 2002/002169 | 1/2002 |
| WO | WO 2002/032486 | 4/2002 |
| WO | WO 2004/024429 | 3/2004 |
| WO | WO 2004/026382 | 4/2004 |
| WO | WO 2005/011785 | 2/2005 |
| WO | WO 2005/021076 | 3/2005 |
| WO | WO 2006/107818 | 10/2006 |
| WO | WO 2006/107818 A2 | 10/2006 |
| WO | WO 2010/028427 A1 | 3/2010 |
| WO | 2020/032808 A1 | 2/2020 |
| WO | WO 2020/178746 | 9/2020 |
| WO | WO 2021/016662 | 2/2021 |
| WO | WO 2021/101780 | 5/2021 |
| WO | WO 2021/152526 | 8/2021 |
| WO | WO 2022/249073 | 12/2022 |
| WO | WO 2022/249117 A1 | 12/2022 |

OTHER PUBLICATIONS

Melikov, A. K. et al. "Accuracy Limitations for Low-Velocity Measurements and Draft Assessment Rooms" HVAC & R Research 13(6), Nov. 2007.

Search Report in corresponding Internaitonal Patent Application No. PCT/IB2022/054939, dated Aug. 24, 2022, in 4 pages.

Written Opinion in corresponding Internaitonal Patent Application No. PCT/IB2022/054939, dated Aug. 24, 2022, in 6 pages.

International Preliminary Report on Patentability in corresponding

(56) References Cited

OTHER PUBLICATIONS

Internaitonal Patent Application No. PCT/IB2022/054939, dated Nov. 21, 2023, in 7 pages.

* cited by examiner

CONTROL OF COMPONENTS OF A BREATHING ASSISTANCE APPARATUS

TECHNICAL FIELD

The present disclosure relates to control of components of breathing assistance apparatuses.

BACKGROUND ART

Breathing assistance apparatuses are used to deliver a flow of gas to patients in various environments (such as hospital, medical facility, residential care, or home environments). A breathing assistance apparatus (e.g. a flow therapy apparatus) may include an oxygen inlet that enables the respiratory apparatus to deliver supplemental oxygen with the flow of gas. A breathing assistance apparatus may also (or alternatively) include a humidification apparatus that enables the respiratory apparatus to deliver heated and humidified gases. A breathing assistance apparatus may allow adjustment of, and control over, characteristics of the gases flow. These characteristics may include for example flow rate, temperature, gas concentration (such as supplemental oxygen concentration), humidity, and pressure, etc.

Patients suffering from various health conditions and diseases can benefit from breathing assistance (for example respiratory therapy). In at least one form, the respiratory therapy may be oxygen therapy. For example, a patient suffering from chronic obstructive pulmonary disease (COPD), pneumonia, asthma, bronchopulmonary dysplasia, heart failure, cystic fibrosis, sleep apnea, lung disease, trauma to the respiratory system, acute respiratory distress, and/or other conditions or diseases can benefit from respiratory therapy. Similarly, patients receiving pre- and post-operative oxygen delivery can also benefit from respiratory therapy.

SUMMARY

In an aspect of the disclosure there is provided a breathing assistance apparatus comprising:

a flow generator configured to generate a flow of gases, a humidifier configured to be pneumatically connected to the flow generator and to humidify the flow of gases generated by the flow generator, wherein the humidifier comprises a heater, wherein the apparatus is configured to be connected to a conduit that conveys the flow of gases, a battery, wherein the apparatus is configured to be powered by the battery or a mains power supply, a controller configured to control the heater of the humidifier according to at least a first control scheme and a second control scheme, wherein when the apparatus is powered by the battery the controller is configured to control the heater of the humidifier according to the first control scheme, the first control scheme comprising providing the heater of the humidifier with a high frequency pulse-width modulation signal, and wherein when the apparatus is powered by the mains power supply the controller is configured to control the heater of the humidifier according to the second control scheme, the second control scheme comprising providing the heater of the humidifier with a low frequency pulse-width modulation signal, and wherein the frequency of the high frequency pulse-width modulation signal is greater than the frequency of the low frequency pulse-width modulation signal.

In an aspect of the disclosure there is provided a breathing assistance apparatus comprising:

a flow generator configured to generate a flow of gases, a humidifier configured to be pneumatically connected to the flow generator and to humidify the flow of gases generated by the flow generator, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller configured to control the heater of the conduit according to at least a first control scheme and a second control scheme, wherein when the apparatus is powered by the battery the controller is configured to control the heater of the conduit according to a first control scheme, the first control scheme comprising controlling the heater of the conduit by analog control, and wherein when the apparatus is powered by the mains power supply the controller is configured to control the heater of the conduit according to a second control scheme, the second control scheme comprising controlling the heater of the conduit by digital control (optionally digital control comprises pulse-width modulation).

In an aspect of the disclosure there is provided a breathing assistance apparatus comprising:

a flow generator configured to generate a flow of gases, a humidifier configured to be pneumatically connected to the flow generator and to humidify the flow of gases generated by the flow generator, wherein the humidifier comprises a heater, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller configured to control the heater of the conduit according to at least a first control scheme and a second control scheme, wherein when the apparatus is powered by the battery the controller is configured to control the heater of the conduit and the heater of the humidifier according to a first control scheme, the first control scheme comprising controlling the heater of the conduit by analog control and providing the heater of the humidifier with a high frequency pulse-width modulation signal, and wherein when the apparatus is powered by a mains power supply the controller is configured to control the heater according to a second control scheme, the second control scheme comprising controlling the heater of the conduit by digital control (optionally by providing a pulse-width modulation signal) and providing the heater of the humidifier with a low frequency pulse-width modulation signal, and wherein the frequency of the high frequency pulse-width modulation signal is greater than the frequency of the low frequency pulse-width modulation signal.

In an aspect of the disclosure there is provided a breathing assistance apparatus comprising:

a flow generator configured to generate a flow of gases, a humidifier configured to be pneumatically connected to the flow generator and to humidify the flow of gases generated by the flow generator, wherein the humidifier comprises a heater, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller configured to control the heater of the conduit and the heater of the humidifier according to at least a first control scheme and a second control scheme, wherein when the apparatus is powered by the battery the controller is configured to control the heater of the conduit and the heater of the humidifier according to a first control scheme, the first control scheme comprising controlling the heater of the conduit by analog control and controlling the heater of the humidifier by digital control, and wherein when the apparatus is powered by the mains power supply the controller is configured to control the heater according to a second control scheme, the second control scheme comprising controlling the heater of the conduit and the heater of the humidifier by digital control.

In an aspect of the disclosure there is provided a breathing assistance apparatus comprising:

a humidifier configured to be pneumatically connected to a flow generator and to humidify the flow of gases generated by the flow generator, wherein the humidifier comprises a heater, wherein the apparatus is configured to be connected to a conduit that conveys the flow of gases, a battery, wherein the apparatus is configured to be powered by the battery or a mains power supply, a controller configured to control the heater of the humidifier according to at least a first control scheme and a second control scheme, wherein when the apparatus is powered by the battery the controller is configured to control the heater of the humidifier according to the first control scheme, the first control scheme comprising providing the heater of the humidifier with a high frequency pulse-width modulation signal, and wherein when the apparatus is powered by the mains power supply the controller is configured to control the heater of the humidifier according to the second control scheme, the second control scheme comprising providing the heater of the humidifier with a low frequency pulse-width modulation signal, and wherein the frequency of the high frequency pulse-width modulation signal is greater than the frequency of the low frequency pulse-width modulation signal.

In an aspect of the disclosure there is provided a breathing assistance apparatus comprising:

a humidifier configured to be pneumatically connected to a flow generator and to humidify the flow of gases generated by the flow generator, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller configured to control the heater of the conduit according to at least a first control scheme and a second control scheme, wherein when the apparatus is powered by the battery, the controller is configured to control the heater of the conduit according to a first control scheme, the first control scheme comprising controlling the heater of the conduit by analog control, and wherein when the apparatus is powered by the mains power supply the controller is configured to control the heater of the conduit according to a second control scheme, the second control scheme comprising controlling the heater of the conduit by digital control (optionally digital control comprises pulse-width modulation).

In an aspect of the disclosure there is provided a breathing assistance apparatus comprising:

a humidifier configured to be pneumatically connected to a flow generator and to humidify the flow of gases generated by the flow generator, wherein the humidifier comprises a heater, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller configured to control the heater of the conduit according to at least a first control scheme and a second control scheme, wherein when the apparatus is powered by the battery the controller is configured to control the heater of the conduit and the heater of the humidifier according to a first control scheme, the first control scheme comprising controlling the heater of the conduit by analog control and providing the heater of the humidifier with a high frequency pulse-width modulation signal, and wherein when the apparatus is powered by a mains power supply the controller is configured to control the heater according to a second control scheme, the second control scheme comprising controlling the heater of the conduit by digital control (optionally by providing a pulse-width modulation signal) and providing the heater of the humidifier with a low frequency pulse-width modulation signal, and wherein the frequency of the high frequency pulse-width modulation signal is greater than the frequency of the low frequency pulse-width modulation signal.

In an aspect of the disclosure there is provided a breathing assistance apparatus comprising:

a humidifier configured to be pneumatically connected to a flow generator and to humidify the flow of gases generated by the flow generator, at least one heater, wherein the apparatus is configured to be connected to a conduit that conveys the flow of gases, a battery, wherein the apparatus is configured to be powered by the battery or a mains power supply, a controller configured to control the at least one heater according to at least a first control scheme and a second control scheme, wherein when the apparatus is powered by the battery the controller is configured to control the heater according to a first control scheme, the first control scheme comprising controlling the heater by analog control, and wherein when the apparatus is powered by the mains power supply the controller is configured to control the heater according to a second control scheme, the second control scheme comprising controlling the heater by digital control (optionally digital control comprises pulse-width modulation).

The at least one heater may comprise a heater of the conduit configured to heat the flow of gases within the conduit.

The at least one heater may comprise a heater of the humidifier.

Controlling the at least one heater by digital control may comprise providing a pulse-width modulation signal to the heater of the conduit.

The frequency of the pulse-width modulation signal may be less than about 20 Hz, or about 20 Hz to about 1 kHz.

The controller may control the duty cycle of pulse-width modulation signal provided to the at least one heater by the second control scheme according to a humidification control algorithm.

The controller may control the duty cycle of the pulse-width modulation signal provided to the at least one heater by the second control scheme based on one or more therapy parameters (optionally the one or more therapy parameters is a therapy temperature of the gases provided to the user).

The controller may control the duty cycle of the pulse-width modulation signal provided to the at least one heater by the second control scheme based on a desired end of conduit temperature of the flow of gases in the conduit.

The duty cycle of the pulse-width modulation signal may be based on a desired power of the at least one heater.

The controller may be configured to measure the power provided to the at least one heater and control the duty cycle of the pulse-width modulation signal based on the measured power provided to the at least one heater and the desired power of the at least one heater.

The first control scheme may comprise providing the at least one heater with a low frequency pulse-width modulation signal, and in the second control scheme comprises providing the at least one heater with a high frequency pulse-width modulation signal, and wherein the frequency of the high frequency pulse-width modulation signal is greater than the frequency of the low frequency pulse-width modulation signal.

In an aspect of the disclosure there is provided a breathing assistance apparatus comprising:

a humidifier configured to be pneumatically connected to a flow generator and to humidify the flow of gases generated by the flow generator, wherein the humidifier comprises a heater, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller configured to control the heater of the conduit and the heater of the humidifier according to at least a first control scheme and a second control scheme, wherein when the apparatus is powered by the battery the controller is configured to control the heater of the conduit and the heater of the humidifier according to a first control scheme, the first control scheme comprising controlling the heater of the conduit by analog control and controlling the heater of the humidifier by digital control, and wherein when the apparatus is powered by the mains power supply the controller is configured to control the heater according to a second control scheme, the second control scheme comprising controlling the heater of the conduit and the heater of the humidifier by digital control.

The frequency of the high frequency pulse-width modulation signal may be greater than the frequency of the low frequency pulse-width modulation signal.

The apparatus may comprise a flow generator configured to generate the flow of gases.

The apparatus may be configured to detect whether the apparatus is operating on the battery or the mains power supply.

The apparatus may be configured to operate on a battery supply where no mains power supply is detected.

The apparatus may be configured to operate on a battery supply based on an input from a user (optionally via a user interface).

The apparatus may comprise a battery charger, and wherein the apparatus is configured to charge the battery when the apparatus is powered by a mains power supply (and optionally when the mains power supply voltage is above a threshold) and the battery is not fully charged (and optionally when the battery charge is below a charge threshold).

The apparatus may comprise a mains power supply conversion circuit, the mains power supply conversion circuit configured to convert the mains power supply to a low DC voltage (optionally about 3 Volts DC to about 60 Volts DC).

The apparatus may comprise a battery conversion circuit, the battery conversion circuit configured to convert the battery supply to a low DC voltage (optionally about 3 Volts DC to about 60 Volts DC).

The battery may be located in the apparatus (and optionally a housing of the apparatus).

The battery comprises at least one battery.

The battery may be configured to connectable and disconnectable from the apparatus (and optionally a housing of the apparatus).

The battery may not connectable and disconnectable from the apparatus (and optionally a housing of the apparatus).

The battery may be part of a battery module.

The battery module may comprise a battery detect pin and/or a battery detect port.

The battery detect pin may comprises a pull up or pull down resistor connected to the battery detect pin.

The battery module may comprises one or more memory elements, the one or more memory elements configured to store one or more battery parameters.

The battery parameters may comprise:

a) The battery expiry date
b) Battery cell states
c) Battery charge states
d) The number of charge and discharge cycles
e) Battery capacity
f) A voltage of the battery
g) A current output of the battery
h) A temperature of the battery
i) Any combination of a)-h).

The apparatus may comprise one or more supply rail capacitors.

The supply rail capacitors may be configured to be located:

a) at an output of the battery
b) at an output of the mains power supply c) at an output of the one or more battery or mains power supply conversion circuits d) any combination of a)-c).

The frequency of the low frequency pulse-width modulation signal of the first control scheme is less than about 20 Hz, or about 20 Hz to about 1 kHz.

The frequency of the high frequency pulse-width modulation signal of the second control scheme is about 25 kHz, or about 1 kHz to about 50 KHz.

The frequency of the high frequency pulse-width modulation signal may be about 1250 times greater than the frequency of the low frequency pulse-width modulation signal.

The frequency of the high frequency pulse-width modulation signal may be an order of magnitude greater than the frequency of the low frequency pulse-width modulation signal.

The frequency of the high frequency pulse-width modulation signal may be about 50 to about times 2000 times greater than the frequency of the low frequency pulse-width modulation signal.

The controller may control the duty cycle of the low frequency pulse-width modulation signal and/or the high frequency pulse-width modulation signal according to a humidification control algorithm.

The controller may control the duty cycle of the low frequency pulse-width modulation signal and/or the high frequency pulse-width modulation signal based on one or more therapy parameters (optionally the one or more therapy parameters is a therapy humidity level, and optionally the therapy humidity level a relative or absolute humidity, or a dew point.

The controller may control the duty cycle of the low frequency pulse-width modulation signal and/or the high frequency pulse-width modulation signal based on a desired power of the heater of the humidifier.

The controller may be configured to measure the power provided to the heater of the humidifier and control the duty cycle of the low frequency pulse-width modulation signal and/or the high frequency pulse-width modulation signal based on the measured power provided to the heater of the humidifier and the desired power of the heater of the humidifier.

The controller may control the duty cycle of the low frequency pulse-width modulation signal and/or the high frequency pulse-width modulation signal based on a desired temperature of the heater of the humidifier.

The desired power requirement and/or desired temperature may be based on one or more therapy parameters of the apparatus.

Controlling the heater of the conduit by digital control may comprise providing a pulse-width modulation signal to the heater of the conduit.

The frequency of the pulse-width modulation signal may be less than about 20 Hz, or about 20 Hz to about 1 kHz.

The controller may control the duty cycle of pulse-width modulation signal provided to the heater of the conduit by the second control scheme according to a humidification control algorithm.

The controller may control the duty cycle of the pulse-width modulation signal provided to the heater of the conduit by the second control scheme based on one or more therapy parameters (optionally the one or more therapy parameters is a therapy temperature of the gases provided to the user).

The controller may control the duty cycle of the pulse-width modulation signal provided to the heater of the conduit by the second control scheme based on a desired end of conduit temperature of the flow of gases in the conduit.

The duty cycle of the pulse-width modulation signal may be based on a desired power of the heater of the conduit.

The controller may be configured to measure the power provided to the heater of the conduit and control the duty cycle of the pulse-width modulation signal based on the measured power provided to the heater of the conduit and the desired power of the heater of the conduit.

Controlling the heater of the conduit by analog control comprises may be by providing an analog control signal to the heater of the conduit and/or the heater of the humidifier.

Controlling the heater of the conduit by analog control may comprise providing a voltage signal to the heater of the conduit.

The analog control signal may be a voltage signal or a current signal.

The analog control signal may be generated by voltage modulation, current modulation, or resistance modulation.

The controller may control the analog control signal provided to the heater of the conduit based on one or more therapy parameters (optionally the one or more therapy parameters is a therapy temperature of the gases provided to the user).

The controller may control the voltage signal provided to the heater of the conduit based on one or more therapy parameters (optionally the one or more therapy parameters is a therapy temperature of the gases provided to the user).

The analog control signal may be controlled based on a desired power of the heater of the conduit.

The voltage signal may be controlled based on a desired power of the heater of the conduit.

The controller may be configured to measure the power provided to the heater of the conduit, and the analog control signal is controlled based on the measured power provided to the heater conduit and a desired power of the heater of the conduit.

The controller may be configured to measure the power provided to the heater of the conduit, and the voltage signal is controlled based on the measured power provided to the heater conduit and a desired power of the heater of the conduit.

The voltage signal may have a quadratic relationship with an input power (for example the measured power provided to the heater conduit).

The analog control signal may be controlled based on a desired end of conduit temperature of the flow of gases in the conduit.

The voltage signal may be controlled based on a desired end of conduit temperature of the flow of gases in the conduit.

The apparatus may comprise analog control circuitry.

The analog control signal may be controlled by the analog control circuitry.

The voltage signal may be controlled by the analog control circuitry.

The analog signal may be controlled by one of more voltage converters of the analog control circuitry.

The one or more voltage converters may comprise:

a) A step-down converter b) A DC-DC converter c) A step-up converter d) A boost converter e) A half bridge converter f) A flyback converter g) A push-pull converter h) A switching converter i) A switching regulator
j) A linear regulator
k) A linear converter
l) A buck converter
m) A transformer
n) Any combination of a)-m).

The voltage signal may be controlled by one of more voltage converters of the analog control circuitry.

The one or more voltage converters may comprise:

a) A step-down converter
b) A DC-DC converter
c) A switching regulator
d) A linear regulator
e) A buck converter
f) A transformer
g) Any combination of a)-f).

When the apparatus is controlling the heater of the conduit according to a second control scheme the analog control circuitry may be disabled.

The apparatus may comprise digital control circuitry configured to generate the pulse-width modulation signal for the heater of the conduit and/or the high frequency pulse-width modulation signal and/or the low frequency pulse-width modulation signal.

The digital control circuitry may comprise one or more switching circuits.

The digital control circuitry may comprise one or more pulse-width modulation drivers.

The digital control circuitry may comprise a heater of the humidifier pulse-width modulation driver configured to generate the high frequency pulse-width modulation signal and the low frequency pulse-width modulation signal.

The digital control circuitry may comprise a heater of the conduit pulse-width modulation driver configured to generate the pulse-width modulation signal.

When the apparatus is controlling the heater of the conduit according to a first control scheme the heater of the conduit pulse-width modulation driver may be disabled.

The heater of the humidifier may comprise a heater plate, and the heater plate is configured to heat a fluid in a humidification chamber to humidify the flow of gases.

The heater of the humidifier may comprise an electrically conductive heating element.

The heater of the conduit may comprise a heater wire.

The heater of the conduit may comprise an electrically conductive heating element.

The heater wire may be:

a) in a lumen of the conduit,
b) within the wall of the conduit
c) embedded in a wall of the conduit
d) embedded in a bead which forms the breathing conduit optionally, the bead is configured to provide structural support to the conduit.
e) located on an external surface of the conduit
f) any combination of a)-e).

The at least one heater may be primarily a resistive load.

The apparatus may comprise a housing, and the flow generator and/or humidifier are located in the housing (optionally a single housing).

The apparatus may comprise a gases inlet and a gases outlet, wherein the conduit is configured to be connected to the gases outlet.

When the apparatus is initially powered by the battery the controller may be configured to:

disable the heater of the humidifier and/or the heater of the conduit, and subsequently, control the heater of the humidifier and/or the heater of the conduit to a desired value or a percentage of a desired value.

Disabling the humidifier heater and/or the heater of the conduit may comprise providing disabling control circuitry and/or providing an off control signal.

The apparatus may be configured to control the heater of the humidifier and/or the heater of the conduit to a desired value or a percentage of the desired value after a predetermined amount of time.

The controller may be configured to the control the heater of the humidifier and/or the heater of the conduit to the desired value or a percentage of the desired value, at, or below a predetermined rate.

When the apparatus is initially powered by the battery the controller may be configured to prioritise delivery of power to the flow generator over the heater of the humidifier and/or the heater of the conduit.

The battery may have a power budget indicating the power able to be supplied by the battery, wherein the power budget is allocated to the flow generator in preference to the heater of the humidifier and/or the heater of the conduit.

The power delivered to the heater of the humidifier and/or the heater of the conduit may be based on a power remaining from the power budget, wherein the power remaining from the power budget is the power budget less the power required to power the flow generator.

If the power remaining is greater than a combined desired power of the heater of the humidifier and/or the heater of the conduit, then the controller may be configured to reduce the power provided to the heater of the humidifier and/or the heater of the conduit (optionally to the remaining power budget).

When the apparatus is initially powered by the battery the controller may be configured to disable the heater of the humidifier and/or the conduit when the battery charge reaches a threshold.

The threshold may be about 5% to about 40%, or about 10% to about 30% or about 20%.

A breathing assistance apparatus comprising:

a humidifier configured to be pneumatically connected to a flow generator and to humidify the flow of gases generated by the flow generator, wherein the humidifier comprises a heater, a battery, wherein the apparatus is configured to be powered by the battery or a mains power supply, a controller configured to control the heater of the humidifier according to at least a first control scheme and a second control scheme, wherein when the apparatus is powered by the battery, the controller is configured to control the heater of the humidifier according to a first control scheme, the first control scheme comprising controlling the heater of the humidifier by analog control, and wherein when the apparatus is powered by the mains power supply, the controller is configured to control the heater of the humidifier according to a second control scheme, the second control scheme comprising controlling the heater of the humidifier by digital control (optionally digital control comprises pulse-width modulation).

In an aspect of the disclosure there is provided a breathing assistance apparatus comprising:

a humidifier configured to be pneumatically connected to a flow generator and to humidify the flow of gases generated by the flow generator, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller configured to control the heater of the humidifier according to at least a first control scheme and a second control scheme, wherein when the apparatus is powered by the battery the controller is configured to control the heater of the conduit according to the first control scheme, the first control scheme comprising providing the heater of the conduit with a high frequency pulse-width modulation signal, and wherein when the apparatus is powered by the mains power supply, the controller is configured to control the heater of the conduit according to the second control scheme, the second control scheme comprising providing the heater of the conduit with a low frequency pulse-width modulation signal, and wherein the frequency of the high frequency pulse-width modulation signal is greater than the frequency of the low frequency pulse-width modulation signal.

In an aspect of the disclosure there is provided a breathing assistance apparatus comprising:

a humidifier configured to be pneumatically connected to a flow generator and to humidify the flow of gases generated by the flow generator, wherein the humidifier comprises a heater, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller, wherein when the apparatus is initially powered by the battery the controller is configured to:

disable the heater of the humidifier and/or the heater of the conduit, and subsequently, control the heater of the humidifier and/or the heater of the conduit to a desired value or a percentage of a desired value.

In an aspect of the disclosure there is provided a breathing assistance apparatus comprising:

a humidifier configured to be pneumatically connected to a flow generator and to humidify the flow of gases generated by the flow generator, wherein the humidifier comprises a heater, wherein the apparatus is configured to be connected to a conduit that conveys the flow of gases, wherein the conduit comprises a heater of the conduit configured to heat the flow of gases within the conduit, a battery, wherein the apparatus is configured to be powered by the battery or a mains power supply, a controller, wherein when the apparatus is initially powered by the battery the controller is configured to prioritise delivery of power to the flow generator over the heater of the humidifier and/or the heater of the conduit.

In an aspect of the disclosure there is provided a humidifier configured to humidify a flow of gases, the humidifier comprising:

a heater, a battery, wherein the humidifier is configured to be powered by the battery or a mains power supply, a controller configured to control the heater according to at least a first control scheme and a second control scheme, wherein when the humidifier is powered by the battery the controller is configured to control the heater of the humidifier according to the first control scheme, the first control scheme comprising providing the heater of the humidifier with a high frequency pulse-width modulation signal, and wherein when the apparatus is powered by the mains power supply the controller is configured to control the heater according to the second control scheme, the second control scheme comprising providing the heater with a low frequency pulse-width modulation signal, and wherein the frequency of the high frequency pulse-width modulation signal is greater than the frequency of the low frequency pulse-width modulation signal.

In an aspect of the disclosure there is provided a humidifier configured to humidify a flow of gases, the humidifier comprising:

at least one heater, wherein the humidifier is configured to be connected to a conduit that conveys the flow of gases, a battery, wherein the apparatus is configured to be powered by the battery or a mains power supply, a controller configured to control the at least one heater according to at least a first control scheme and a second control scheme, wherein when the humidifier is powered by the battery the controller is configured to control the at least one heater according to a first control scheme, the first control scheme comprising controlling the at least one heater by analog control, and wherein when the humidifier is powered by the mains power supply the controller is configured to control the at least one heater according to a second control scheme, the second control scheme comprising controlling the at least one heater by digital control (optionally digital control comprises pulse-width modulation).

The at least one heater may comprise a heater of the conduit configured to heat the flow of gases within the conduit.

The at least one heater may comprise a heater of the humidifier.

In another aspect there is provided a surgical humidifier, the surgical humidifier may have any of the features as described with relation to the breathing assistance apparatus in any of the above aspects.

It will be appreciated that any of the above statements may be combined with any one or more other statements.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

Some embodiments of this disclosure may also be said broadly to consist or comprised in the parts, elements and features referred to or indicated in the specification of the application, individually or collectively, and any or all combinations of any two or more said parts, elements or features, and where specific integers are mentioned herein which have known equivalents in the art to which this disclosure relates, such known equivalents are deemed to be incorporated herein as if individually set forth.

The term "comprising" as used in this specification means 'including'. When interpreting each statement in this specification that includes the term 'comprising', features other than that or those prefaced by the term may also be present. Related terms such as 'comprise' and 'comprises' are to be interpreted in the same manner.

The term request when used in the context of a controller may refer to the controller sending a signal to a component to instruct the component to perform one or more actions.

As used herein the term '(s)' following a noun means the plural and/or singular form of that noun.

As used herein the term 'and/or' means 'and' or 'or', or where the context allows both.

The disclosure discloses the foregoing and also envisages constructions of which the following gives examples only.

It will be appreciated that when a list set out, the disclosure includes any combination of items in the list.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION

Figure 1:
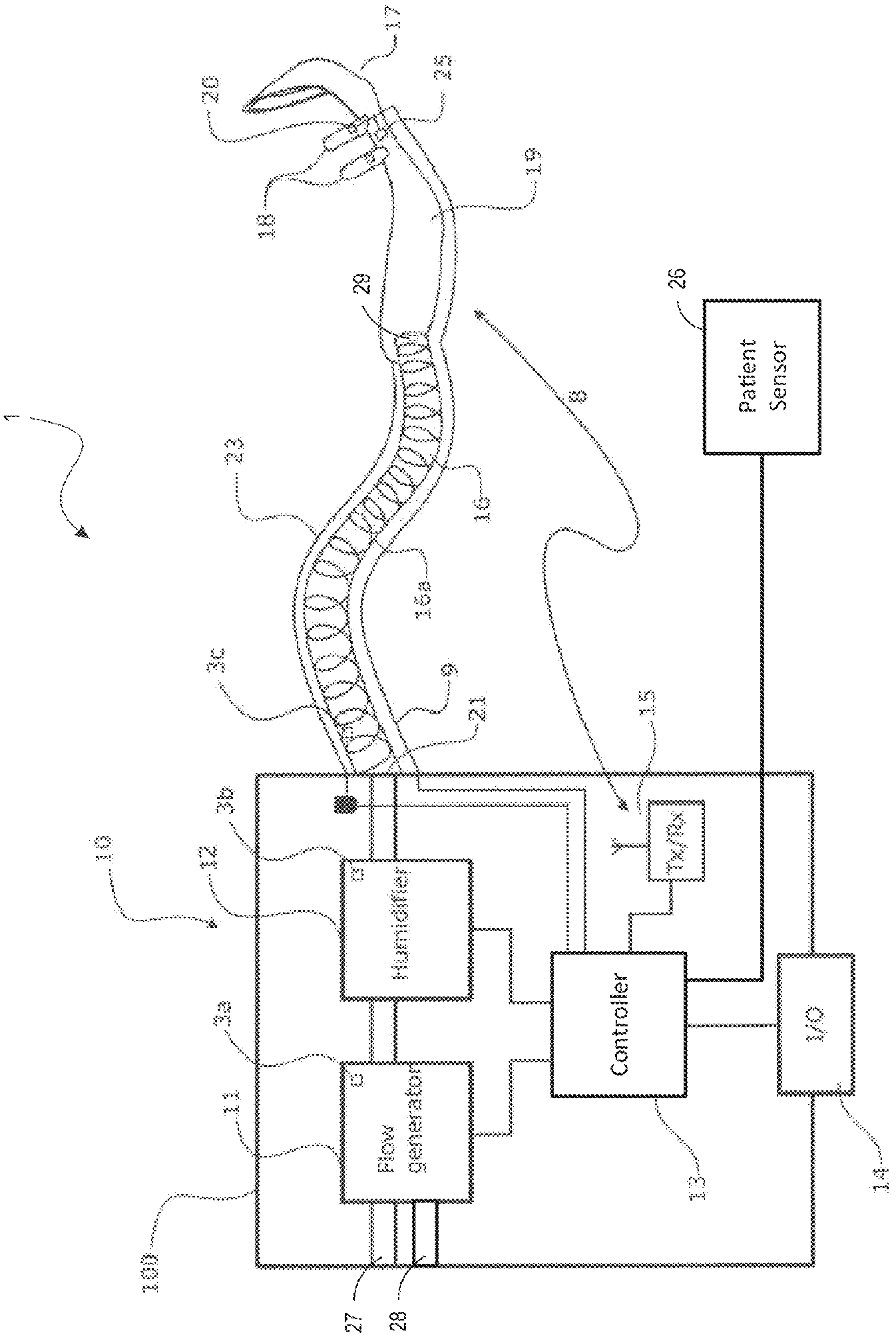
FIG. 1 shows in diagrammatic form a breathing assistance apparatus.

A breathing assistance apparatus 10 provides therapy to a user for example any combination of: Nasal High Flow (NHF) therapy, Continuous Positive Airway Pressure (CPAP) therapy, Non-Invasive Ventilation (NIV) and Bubble Continuous Positive Airway Pressure (BCPAP) therapy.

In some configurations, the apparatus 10 may be used either during pre-oxygenation or during anaesthesia. In some configurations, the apparatus 10 may be used during any other medical procedure where the patient is apnoeic or otherwise where respiratory function might be diminished or at risk of being diminished.

During operation the apparatus 10 may operate from a number of power sources. In some cases, the apparatus 10 may be powered by a mains power supply (for example, from the power grid). In some cases, the apparatus 10 may be powered by a battery.

The electrical characteristics of a mains power supply may be considerably different from the electrical characteristics of a battery. For example, the mains power supply may be at a mains voltage (i.e., 100 volts to about 240 volts) and provided as alternating current, while the battery may be at a voltage of less than 100 volts and provided as direct current. Further, the rated power delivery of the battery may be significantly lower than that of the mains power supply.

If the power drawn by the apparatus exceeds the rated power delivery of the battery, the battery may overheat, be damaged.

Further, if the power drawn by the apparatus transiently exceeds or consistently exceeds the rated power of the battery, the voltage supply of the battery may decrease—which may cause damage to the apparatus, or make measurements or calculations undertaken by the apparatus unreliable. In some cases, the voltage may decrease below a threshold required by the apparatus to function, and the apparatus may power off.

A further consideration is the electromagnetic interference generated by the apparatus. The generation of electromagnetic interference may be as a consequence of high frequency switching of components in the apparatus. The generation of electromagnetic interference may be worse in the heater of the conduit (for example, if the heater of the conduit is a wire that extends down a length of the conduit) as the heater of the conduit may extend along a length of the conduit and therefore increase electromagnetic interference (for example, the strength of an interfering electromagnetic field) by behaving, in part, like an antenna.

One mechanism for the increase in electromagnetic interference due to the heater of the conduit, is as the wavelength of the switching signal approaches a multiple, or integer multiple, of the length of the heater of the conduit, the strength of the electromagnetic interference (EMI) increases. This effect may be more pronounced as a consequence of high frequency switching of the heater of the conduit as the wavelength of the switching signal is shorter and approaches a multiple of the length of the heater, causing increased EMI (depending on the length of the heater of the conduit). This is less of an issue with relatively lower frequency switching of the heater of the conduit as the wavelengths are much relatively longer and relatively further away from a multiple of the length of the heater of the conduit.

Electromagnetic interference may be at least partially mitigated by providing shielding to the heater of the conduit; however this increases cost and complexity of the conduit.

Electromagnetic interference may interfere with operation of the apparatus 10 (for example internal controllers, integrated circuits or sensors) as well as other devices in the vicinity of the apparatus.

The current disclosure provides for control of heaters of the apparatus based on the type of power supply (and the associated electrical characteristics)—for example, by decreasing the peak power drawn, while managing the electromagnetic interference generated by the apparatus 10 and providing therapy to a user.

As described in more detail below, the apparatus 10 may comprise a heater of the humidifier (for example, a heater plate) and a heater of the conduit (for example, a heater wire).

The heater may comprise one or more heating elements. It will be appreciated that other heater types as known in the art may be utilised.

When the apparatus 10 is powered by a mains power supply (or, for example, another non-peak power limited supply as described in more detail below) the apparatus 10 may control the heater of the humidifier and heater of the conduit by digital control (for example, by pulse-width modulation).

The pulse-width modulation control may be by providing the heater of the humidifier and/or the heater of the conduit with a pulse-width modulation signal (as described in more detail below).

The term pulse-width modulation signal may be used interchangeably with the term pulse-width modulated signal.

The pulse-width modulation signal may be provided to the heater of the humidifier and/or the heater of the conduit to provide power to the heater of the humidifier and/or the heater of the conduit.

When the apparatus 10 is powered by a mains power supply, the frequency of the pulse-width modulation signal may be provided at a relatively low frequency to decrease the electromagnetic interference generated by the device (for example, as a low frequency pulse-width modulation signal.)

However, when the apparatus 10 is powered by a battery (or, for example, another peak power limited supply as described in more detail below) using the same digital control (for example, pulse-width modulation) for the heater of the humidifier and the heater of the conduit may cause the power rating (for example a power delivery or supply rating) of the battery to be exceeded during the ON portion of the pulse-width modulation signal as the apparatus attempts to draw more power than the battery is capable of providing.

Therefore, when the apparatus 10 is powered by a battery (or, for example, another peak power limited supply as described in more detail below) the frequency of the pulse-width modulation signal may be increased (for example, as a high frequency pulse-width modulation signal). However, this may be counterintuitive as it may increase the electromagnetic interference generated by the apparatus and it may decrease efficiency of the switching circuits (for example, by increasing switching losses of MOSFETs, or other types of transistors in the switching circuits) in the digital control circuitry which generates the pulse-width modulation signal.

The use of a high frequency pulse-width modulation signal in combination with a capacitive energy storage (for example, a supply rail capacitor as described below) allows for the apparatus' peak power demand to be met, without exceeding the battery power rating. For example, the battery may only be required to provide a lower peak power (as the discharging capacitive energy storage will provide additional power during the ON portion of the pulse-width modulation signal.) This approach may be difficult in the context of a low frequency pulse-width modulation signal which would require significantly larger capacitive energy storage as the ON portion of the pulse-width modulation signal would be relatively longer and therefore a greater amount of energy would need to be provided to the apparatus during the ON portion compared with that required with a high frequency pulse-width modulation signal (i.e., as additional power from the capacitive energy store). The larger capacitive energy storage required to provide the additional power may lead to increased cost of the apparatus and increased space requirements due to the larger capacitive energy storage.

Using a low frequency pulse-width modulation signal when operating from a battery may increase the heat generated by the battery, which may lead to increased degradation of the battery, for example as decreased battery life.

The terms "low frequency pulse-width modulation signal" and "high frequency pulse-width modulation signal" are relative terms and may be substituted with the terms "first pulse-width modulation signal" and "second pulse-width modulation signal" (respectively).

When the apparatus 10 is powered by a battery, the apparatus (for example, by the controller 13) may control the heater of the humidifier by providing a high frequency pulse-width modulation signal. This may decrease the peak power drawn from the battery, while still decreasing switching losses and still maintaining the generation of electromagnetic interference below acceptable levels.

If the high frequency pulse-width modulation signal is applied to the heater of the conduit, the resulting electromagnetic interference generated may exceed acceptable levels. Further, the high frequency pulse-width modulation signal may interfere with safety mechanisms designed to detect energy transients or short circuiting of the heater of the conduit. For example, if the safety mechanism is configured to monitor the rate of change of voltage, the high frequency pulse-width modulation signal could cause false triggers. Alternately, the threshold rate of change of voltage for the safety mechanisms is raised, then the safety mechanism may be less effective and the safety risk to a user may increase.

Battery operation of the apparatus 10 may allow for a patient in a hospital setting to be transported between locations in a hospital (for example to a recovery ward) while still providing therapy (and humidified gases). Therapy can therefore be continuously provided before transport (while operating on for example a mains power supply), during transport of the patient (while operating on for example a battery), and after transport (while operating on for example a mains power supply.

Battery operation of the apparatus 10 may allow for a patient in a home setting to be mobile and undertake activities or tasks without having to be confined to a location with a mains power supply while still being provided with therapy.

The disclosure may allow for the apparatus to be operated from a battery for a longer period of time, as the peak power draw is decreased r, which may extend the battery life for a time sufficient to for example transport patients in a hospital setting or allow a patient to undertake activities or tasks which they usually could not if confined to a mains power supply. The battery life may for example be about 45 minutes, and the apparatus may provide therapy (at or close to the desired therapy parameters) during this time.

Providing therapy when powered by a battery may provide comfort and compliance benefits. The disclosure may provide control schemes to allow for humidity to be delivered while also allowing portability.

Providing a therapy humidity to a user may increase patient comfort and compliance with therapy. The provision of humidity also provides additional benefits of improving mucus transport, which is useful in patient with obstructive pulmonary diseases, improving comfort and therefore compliance/acceptance of these therapies.

Decreasing the peak power draw during battery operation may also allow for the use of smaller batteries while still delivering therapy (for example at or close to the desired therapy parameters). The use of relatively smaller battery power supplies may keep the apparatus compact, which may mean the weight and size of the apparatus is not increased by the inclusion of a relatively larger battery. Thus, the disclosure may lead to a more portable and easier to use apparatus. Portability of the apparatus may increase usability of the apparatus in a homecare setting as the apparatus can be more easily moved around the user's house. In a hospital setting portability allows the therapy apparatus to be moved around the hospital with the patient so the patient can continue to receive therapy while being transported.

In the context of a surgical humidifier (as described below in more detail), the disclosure may provide for a system where in the event of a loss of mains power (e.g., a power cut), during transport, or where surgery needs to be provided in an area without an available mains power supply, therapy can still be provided (for example at or close to the desired therapy parameters). The disclosure above is equally applicable to a surgical humidifier.

When the apparatus 10 is powered by a battery, the apparatus may control the heater of the conduit and/or the heater of the humidifier by analog control (for example, by providing a voltage (i.e., an analog-modulated or regulated voltage) across the heater of the conduit and/or the heater of the humidifier.)

Analog control may be implemented by providing the heater of the conduit and/or the heater of the humidifier with analog control signal (as described in more detail below).

In some configurations, the analog control circuitry configured to generate the analog control signal (for example, voltage) provided across the heater of the conduit may generate electromagnetic interference (for example, through the antenna effect as described above, and through switching the control signal) but much less than if high frequency pulse-width modulation is used.

Similarly, with respect to the heater of the humidifier, the analog control circuitry configured to generate the analog control signal (for example, voltage) provided across the heater of the humidifier may generate electromagnetic interference (for example, through switching the digital control signal) but much less than if high frequency pulse-width modulation is used.

Analog control circuitry may be less efficient than digital control due to, for example, additional losses introduced by certain components in some circuit topologies used to generate the analog control signal, e.g., high frequency switching components.

When the apparatus 10 is powered by a battery, the combination of digital control of the heater of the humidifier (with a high frequency pulse-width modulation signal) and analog control of the heater of the conduit may ensure peak power draw from the battery does not exceed the battery rating and ensures generation of electromagnetic interference is maintained below acceptable levels.

In some configurations, when the apparatus 10 is powered by a battery, the combination of analog control of the heater of the conduit and analog control of the heater of the humidifier may ensure peak power draw from the battery does not exceed the battery rating and ensures generation of electromagnetic interference is maintained below acceptable levels.

A breathing assistance apparatus 10 is shown in FIG. 1. The breathing assistance apparatus 10 can comprise a housing 100 (for example as a single housing) that contains one or more of: a flow generator 11, which in some configurations is in the form of a motor/impeller arrangement (for example, a blower), a humidifier 12 pneumatically connected to the flow generator 11, a controller 13, and a user interface 14 (comprising, for example, a display and input device(s) such as button(s), a touch screen, or the like).

Figure 2:
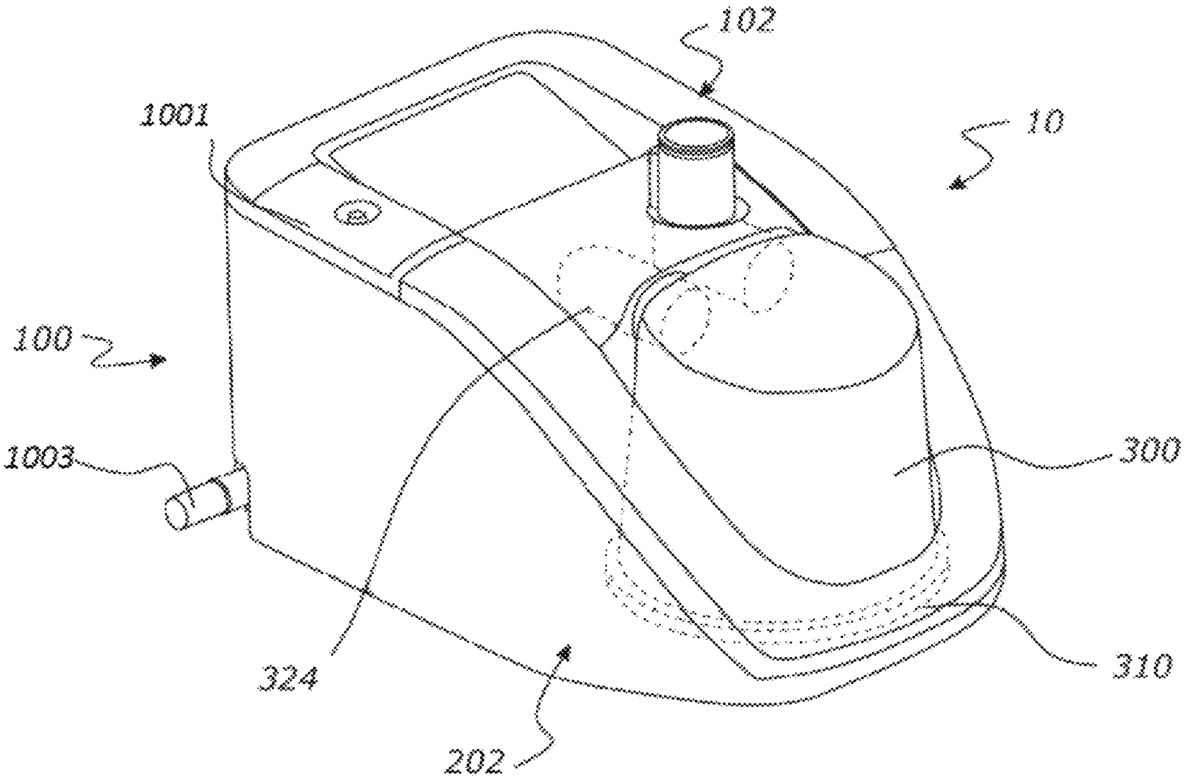
FIGS. 2, 2A and 2B show perspective views of a breathing assistance apparatus.

In FIG. 2, the apparatus 10 shows a housing 100 comprising a flow generator 11 and a humidifier 12 pneumatically connected to the flow generator 11. As shown in FIG. 2, the humidifier 12 and flow generator 11 are integrated into a common housing. This provides a compact device that can be easily moved around or carried to provide mobility. Further the flow generator 11 and humidifier 12 being combined in the same housing allows for simpler set up (i.e., chamber 300 is positioned in the housing).

In some configurations, the breathing assistance apparatus 10 may not comprise a flow generator 11. In this case the apparatus 10 does not generate a flow of gases, and instead is configured to be connected to an external flow generator and configured to humidify the flow of gases from the external flow generator. For example, the breathing assistance apparatus 10 can be used as a stand-alone humidifier to humidify gases flowing through the humidifier. The flow generator may be a wall gas supply (regulated via a flowmeter or rotameter, for example) or a ventilator or other separate flow generator that can be configured to provide one of the therapies described elsewhere in the specification (e.g., NIV, NHF, CPAP, BCPAP, invasive ventilation, etc). The humidifier may include a battery coupled to the humidifier to supply power when mains is unavailable (as a battery supply). In some configurations, the battery may be removably coupled to the apparatus and is rechargeable. The humidifier is pneumatically coupled to a flow generator via a conduit and a separate conduit is coupled to the humidifier to convey humidified gases from the humidifier to a patient.

Figure 2A:
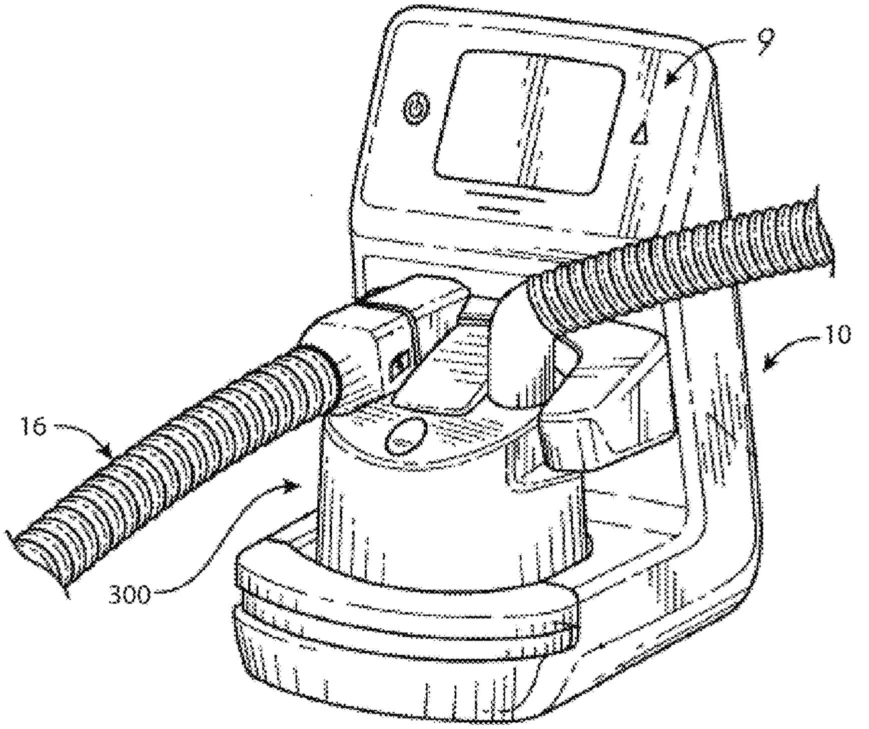
Figure 2B:
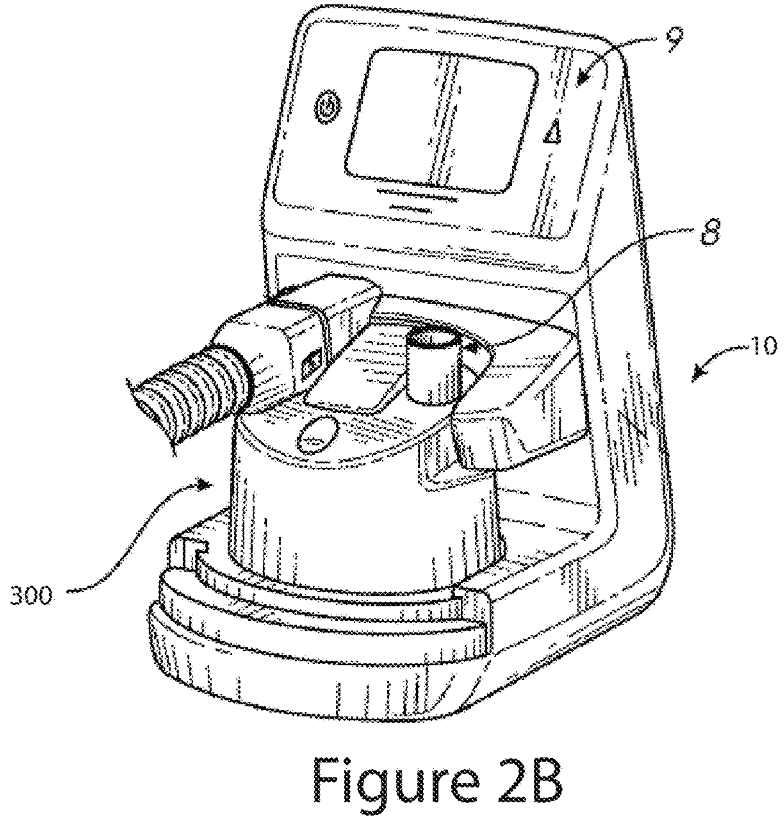

An example of an apparatus 10 as a humidifier (i.e., without a flow generator) is shown in FIGS. 2A and 2B. The apparatus includes a connector that pneumatically connects a conduit 16 (as described in more detail above) to an outlet (as a gases outlet of the apparatus) of a humidification chamber 31. The conduit 16 may be an inspiratory limb of a patient circuit, i.e., configured to deliver humidified gases to a user, such as via a patient interface (not shown). The conduit 16 may have a conduit heater **16*a*** (as, for example, described elsewhere in the specification).

An inlet 8 of the humidification chamber 300 is configured to be fluidly connected to a flow generator positioned remote from the apparatus 10 (for example, by the conduit shown connected to inlet 8 in FIG. 2A).

As shown in FIGS. 2A and 2B, the apparatus 10 further includes a panel 9 which may be used to mount a user display and/or controls. For example, various dials, switches, and other input means may be used to control operation of the device. Additionally, or alternatively, a touch screen display may be used. The user display may display parameters of the system, warnings in the event of any errors or malfunctions, or prompts where user action is required, etc. Where a touch screen display is used, the same display may be used to present information to a user and receive inputs from a user, at least in part (as, for example, described elsewhere in the specification). The humidifier apparatus shown in FIGS. 2A and 2B may comprise multiple sensors. For example, the humidifier 10 may comprise a flow sensor, one or more temperature sensors, one or more pressure sensors and one or more humidity sensors. In one example configuration the humidifier comprises at least a temperature sensor positioned within or adjacent the inlet and a temperature sensor within or adjacent the outlet of the chamber 300. Optionally the humidifier may comprise a flow sensor within or adjacent the outlet of the chamber 300. Additionally, a further flow sensor may be located within or adjacent the inlet 8. Optionally the humidifier may include a single flow sensor located in the inlet or outlet. The humidifier may additionally comprise one or more humidity sensors, that may be arranged within or adjacent either of the inlet or outlet, or in the inlet and outlet. Further there may be additional ambient temperature sensors. The humidifier may also comprise additional sensors associated with the heater e.g., temperature sensors associated with the heater.

In some configurations, the apparatus 10 as shown in FIGS. 2A and 2B may comprise a battery (as discussed in more detail below.)

The battery may be a battery supply. It will be appreciated that the term battery and battery supply can be used interchangeably where context allows.

It also will be appreciated that the battery may be externally located to the apparatus (for example located remotely but electrically connected to the apparatus).

The apparatus 10 may for example be the apparatus as described in WO2015/093989 and WO2015/038014 which are both incorporated by reference in their entirety.

The humidifier 12 can humidify the gases flow and/or heat the gases flow to an appropriate level. The controller 13 can be configured to control the humidifier 12 (for example, by controlling at least a humidifier heater).

The humidifier 12 may comprise a humidification chamber. The humidification chamber may be configured to be removed from the humidifier (for example for replacement, cleaning and/or refilling). Alternatively, the humidification chamber may be non-removable from the humidifier.

The humidification chamber may comprise an autofill mechanism that comprises at least a valve and a float coupled to the valve. The humidification chamber in use can be coupled to water reservoir of water bag to auto fill. Alternatively, the humidification chamber may be manually refilled.

The humidifier 12 may comprise a humidifier heater 310 for example as a heater plate (see FIG. 2). The humidifier heater provides heat to the humidification chamber 300. The liquid in the humidification chamber may be water or another liquid, and/or may comprise a mixture of one or more liquids (for example a mixture of water and a medicament.)

The heater 310 of the humidifier 12 may be an electrically conductive heating element.

The humidifier may also be a surgical humidifier which humidifies a gas (such as carbon dioxide) for use in surgery such as laparoscopic and open surgery.

The surgical humidifier may have any combination of the features of the humidifier as disclosed with respect to the humidifier of FIGS. 2A and 2B.

It will be appreciated that the disclosure may be applied to a surgical humidifier (or other humidifier), and that the disclosure below with respect to the breathing assistance apparatus may be applicable to a surgical humidifier.

The controller 13 can be configured or programmed to control the operation of the breathing assistance apparatus 10. For example, the controller 13 can control components of the breathing assistance apparatus 10, including but not limited to: operating the flow generator 11 to create a flow of gas (gases flow) for delivery to a patient, operating the humidifier 12 (if present) to humidify and/or heat the generated gases flow, controlling a flow of oxygen into the flow generator blower, receiving user input from the user interface 14 for reconfiguration and/or user-defined operation of the breathing assistance apparatus 10, and outputting information (for example, on the display) to the user.

The controller 13 may comprise one or more sub controllers. The sub controllers may each be configured to control one or more components of the apparatus (for example, a flow generator sub controller, and/or a humidifier sub controller and/or a humidifier or conduit heater sub controller). The controller 13 may include a master controller configured to communicate with, and pass commands to the sub controllers.

The controller 13 may include one or more computer processors and associated non-transitory memory or storage mediums storing processor-executable instructions or code. The instructions, when executed by the one or more processors cause the respiratory therapy apparatus to affect the steps and processes described herein.

It will be appreciated that when the specification describes the apparatus 10 undertaking an action, it may be that the controller 13 is controlling one or more components of the apparatus 10 to undertake the action.

It will be appreciated the methods described herein can be executed by the controller (or another processor).

The term breathing assistance apparatus may be used interchangeably with respiratory assistance apparatus, or respiratory therapy apparatus or flow therapy apparatus.

The term breathing assistance system may be used interchangeably with respiratory assistance system, or respiratory therapy system, or flow therapy system.

The term current flow rate may refer to a measurement of a flow rate which has been presently made (for example, at a current time step). It will be appreciated that the term current flow rate is not limited to the latest flow rate determination and could include recently made flow rate determinations (for example, from a previous time step or the most recent flow rate determination), and/or a filtered flow rate determination made based on a series of past measurements (which may optionally include signal filtering and/or processing).

The methods described herein may be embodied as software or a software module as part of control software (for example, computer-readable instructions) that are stored in the controller (or associated memory) and executed by the controller (and/or an associated processor).

In the context of receiving therapy, the user is a patient, however in the context of interacting with the apparatus (for example, interacting with a user interface) the user can be one or more of a patient, healthcare professional (for example, a clinician), or anyone else interested in using the apparatus.

As used herein, a "gases flow" can refer to any flow of gases that may be provided by the breathing assistance apparatus, such as a flow of ambient air, a flow comprising substantially 100% oxygen, a flow comprising some combination of ambient air and oxygen, and/or the like.

A breathing conduit 16 is coupled at one end to a gases outlet 21 in the housing 100 of the breathing assistance apparatus 10. The breathing conduit 16 is coupled at another end to a patient interface 17 such as a non-sealed nasal cannula with a manifold 19 and nasal prongs 18. Additionally, or alternatively, the breathing conduit 16 can be coupled to a face mask, a nasal mask, a nasal pillows mask, an endotracheal tube, a tracheostomy interface, and/or the like.

A breathable conduit may be provided between the breathing conduit 16 and the patient interface 17.

In some configurations, a different conduit type may be connected to the gases outlet 21, for example a disinfection conduit in a disinfection mode. The disinfection mode may be that as described in WO2007/069922 which is incorporated by reference in its entirety.

In disinfection mode the disinfection conduit may be heated to temperatures that may disinfect a gases flow path of the apparatus (for example the disinfection conduit and/or one or more elbows).

The gases flow that is generated by the breathing assistance apparatus 10 may be humidified and delivered to the patient via the breathing conduit 16 and the patient interface 17.

The breathing conduit 16 can have a heater 16*a* to heat the gases flow passing through to the patient. The heater 16*a* can be under the control of the controller 13. In at least one configuration, the heater 16*a* is a heater wire. The breathing conduit 16 and/or patient interface 17 can be considered part of the breathing assistance therapy system. The breathing assistance system 1 may comprise the breathing assistance apparatus 10, breathing conduit 16, and patient interface 17.

The heater 16*a* of the breathing conduit may be located:

a) in a lumen of the breathing conduit 16, b) within the wall of the breathing conduit 16 c) embedded in a wall of the breathing conduit 16 d) embedded in a bead which forms the breathing conduit 16. The bead is configured to provide structural support to the conduit 16.

e) located on an external surface of the breathing conduit 16 f) any combination of a)-e).

The heater 16*a* may extend linearly along the conduit 16 or be helically wrapped around the conduit or be helically wrapped within the conduit.

The heater 16*a* of the breathing conduit 16 may be an electrically conductive heating element (for example, a heater wire).

The controller 13 can control the flow generator 11 to generate a gases flow at the desired flow rate (for example, a therapy flow rate). The controller 13 can also control a supplemental oxygen inlet to allow for delivery of supplemental oxygen.

The controller 13 can also control a humidifier heater in the humidifier 12 and/or the heater 16*a* in the breathing conduit 16 to heat the gas to a desired temperature for a desired level of therapy and/or level of comfort for the patient.

The controller 13 can be provided with or can determine a suitable target temperature of the gases flow. The controller 13 may control the humidifier heater of the humidifier 12 and/or the heater 16*a* of the breathing conduit based on one or more suitable target temperature(s) of the gases flow.

The heater 16*a* of the breathing conduit 16 may be controlled by the controller 13 to reach a desired temperature. The desired temperature may be, or be based on, one or more temperature set points, and/or one or more humidity set points (for example, a therapy humidity).

The humidifier heater of the humidifier 12 may be controlled by the controller 13 to reach a desired temperature. The desired temperature may be, or be based on, one or more temperature set points, and/or one or more humidity set points. The desired temperature may be a therapy parameter.

The controller 13 may control the heater 16*a* of the breathing conduit 16 and/or the humidifier heater of the humidifier 12 to the desired temperature by closed loop control based on the output of one or more sensors.

The one or more temperature set points may relate to one or more therapy parameters of the apparatus for therapy (for example, a dew point or temperature of the gases) or be provided in the memory of the apparatus (for example, a predetermined temperature). Various therapy parameters for various therapies are set out below, however it will be appreciated that when referring to therapy parameters in the specification it can refer to any therapy parameter or any combination of therapy parameters. The therapy parameters may be a parameter of the gases provided to the user by the apparatus during therapy.

One or more therapy parameters may be a therapy humidity level. The therapy humidity level may be a measure indicative of the humidity of the gases provided to the user. For example, the therapy humidity level may be a relative humidity, an absolute humidity, and/or a dew point temperature of the gases.

The apparatus may provide any combination of: Nasal High Flow (NHF) therapy, Continuous Positive Airway Pressure (CPAP) therapy, Non-Invasive Ventilation (NIV) and Bubble Continuous Positive Airway Pressure (BCPAP) therapy. The apparatus may comprise one or more control modes associated with each therapy type. The control modes may be manually selected by the user or automatically selected depending on the components connected to the apparatus (for example dependent on the type of tube and/or patient interface connected to the apparatus). Each control mode may have an associated control scheme for controlling components of the apparatus (for example the flow generator, humidifier heater 310 or conduit heater 16*a*).

The one or more therapy parameters for NHF therapy may comprise any combination of:

a therapy flow rate of the gases provided to the user, a therapy humidity level (for example a relative or absolute humidity, or a dew point)

a therapy oxygen concentration provided to the user, a therapy concentration of an auxiliary gas provided to the user, a therapy temperature of the gases provided to the user (for example).

The one or more therapy parameters for BCPAP therapy may comprise any combination of:

a therapy flow rate of the gases provided to the user, a therapy humidity level (for example a relative or absolute humidity, or a dew point)

a therapy oxygen concentration provided to the user, a therapy concentration of an auxiliary gas provided to the user, a therapy temperature of the gases provided to the user.

The one or more therapy parameters for CPAP therapy may comprise any combination of:

a therapy humidity level (for example a relative or absolute humidity, or a dew point)

a therapy oxygen concentration provided to the user, a therapy temperature of the gases provided to the user.

a therapy concentration of an auxiliary gas provided to the user, a therapy level of pressure support (for example a CPAP pressure) provided to the user a therapy PEEP pressure provided to the user.

The one or more therapy parameters for Bilevel therapy i.e., NIV therapy may comprise any combination of:

a therapy humidity level (for example a relative or absolute humidity, or a dew point)

a therapy oxygen concentration provided to the user, a therapy temperature of the gases provided to the user.

a therapy concentration of an auxiliary gas provided to the user, a therapy IPAP/EPAP pressure (inspiratory positive airway pressure/expiratory positive airway pressure) provided to the user.

The therapy temperature may comprise a therapy temperature at the chamber outlet and/or a therapy temperature at the end of the breathing conduit.

The therapy humidity may be at the chamber outlet or at the end of the breathing conduit.

The therapy humidity level may be a dew point of about 27 degrees Celsius to about 40 degrees Celsius, or about 29 degrees Celsius to about 39 degrees Celsius, or about 31 degrees Celsius to about 38 degrees Celsius, or about 37 degrees Celsius, or an absolute humidity of above about 38 mg H20 or about to 44 mgH2O.

Providing humidity to a user increases patient comfort and compliance with therapy. The provision of humidity also provides additional benefits of improving mucus transport, which is useful in patient with obstructive pulmonary diseases, improving comfort and therefore compliance/acceptance of these therapies.

The user may enter one or more therapy parameters via the user interface.

The desired temperatures may be at end of the breathing conduit 16, at the patient interface, at the gases outlet, a humidification chamber outlet, at any sensor of the apparatus, and/or any combination thereof.

The one or more temperature set points may comprise one or more of:

- a desired dew point (for example a temperature indicative of a desired humidity),
- a predetermined dew point,
- a predetermined temperature,
- a desired temperature.

In some configurations the controller 13 may control the heater **16*a* of the breathing conduit 16 based on a desired temperature of the gases at the patient interface and/or a desired temperature at the end of the breathing conduit 16**.

The apparatus may be powered by a mains power supply (for example, a wired connection with an electrical grid or, for example, a portable electrical generator, distributed generation source, and/or non-portable electrical generators such as hospital back-up generators).

The mains power supply may be an AC power source at a voltage level of about 100 to about 240 $V_{RMS}$, at about 50 to about 60 Hz, depending on the operating region of the apparatus.

In some configurations, mains power supply may be any power supply configured to be connected to the apparatus via the electrical socket 114.

In some configurations, mains power supply may include any power supply which does not have an energy availability and/or capacity constraint (for example, as with a battery).

The apparatus may be powered by a non-peak power limited supply or a peak power limited supply (for example, a battery). Peak power limited in this context refers to the peak power required by the apparatus to operate with full capability even during transient moments of higher power demand.

The apparatus may be powered by an integrated power supply or an external power supply.

Figure 3:
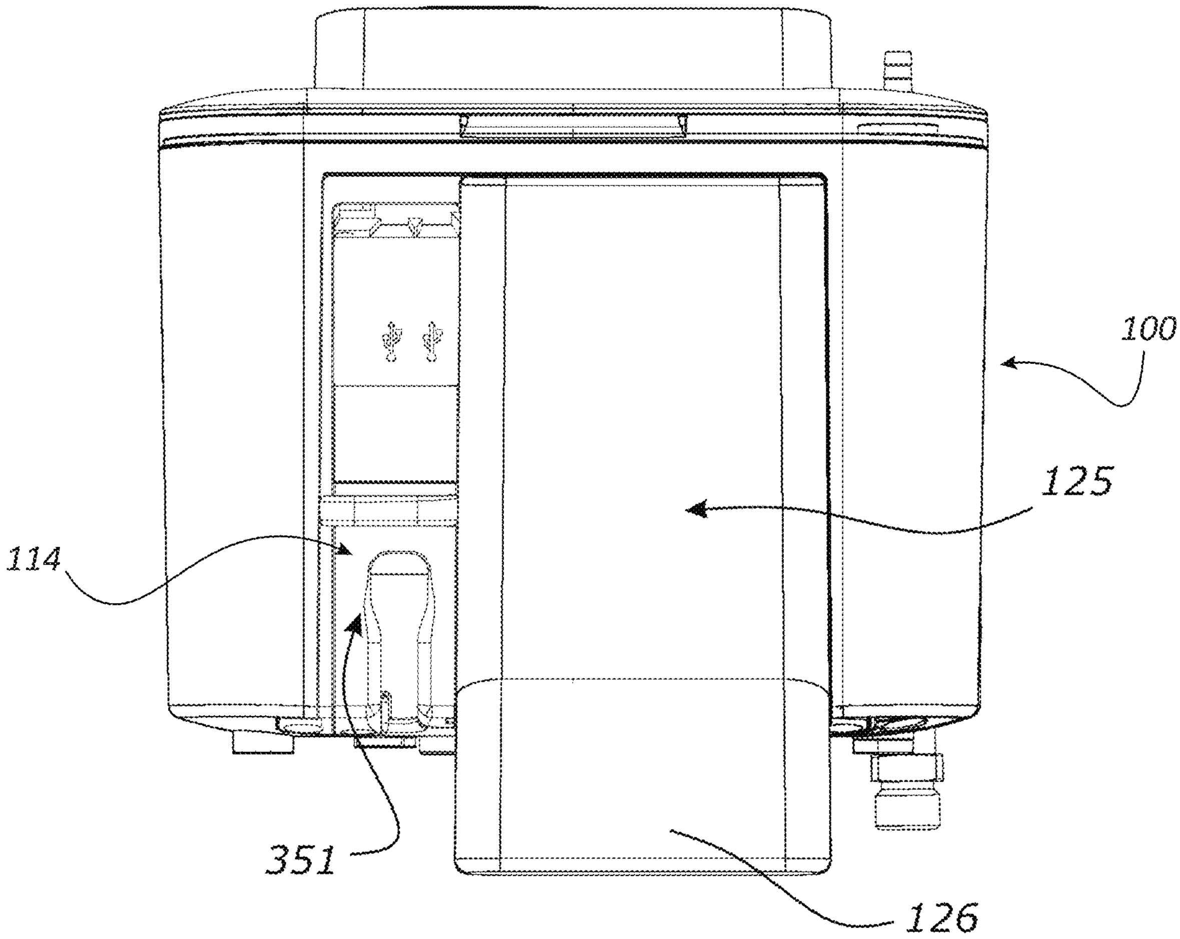
FIG. 3 is a rear perspective view of a breathing assistance apparatus.

In some configurations, for example, as shown in FIG. 3, the apparatus may comprise at least one battery 125 as part of a battery module (with optional battery cover 126). The battery module may be located in the housing of the apparatus, and/or attached externally to the housing of the apparatus (as shown in FIG. 3). It will be appreciated when the term battery is used in the specification it may refer to either the battery itself, or the battery module which comprises the battery.

In some configurations, the battery is removable (as shown in FIG. 3) and optionally connectable and disconnectable from the apparatus 10. Alternatively, the battery is non-removable.

In some configurations, the battery is provided as part of the same housing as the flow generator and/or the humidifier. In some configurations, the battery is provided as connectable and disconnectable to the same housing as the flow generator and/or the humidifier.

Having the battery as part of the housing, or connectable and disconnectable to the housing may allow for the apparatus to be portable compared to other apparatuses (for example larger apparatuses such as ventilators, or those with external battery power sources which are not portable). As described above, portability of the apparatus may increase usability of the apparatus in a homecare setting as the apparatus can be more easily moved around the user's house. In a hospital setting portability allows the therapy apparatus to be moved around the hospital with the patient so the patient can continue to receive therapy while being transported.

The battery module may be the battery supply.

The battery 125 may comprise a plurality of cells that provide a current (i.e., energy) and have a voltage (i.e., an electromotive force) across their terminals.

The battery module may comprise a battery detect pin and/or a battery detect port. The battery detect pin and/or a battery detect port may be configured to communicate with the apparatus that the battery is connected. The battery detect pin may comprise a pull-up or pull-down resistor connected to the battery detect pin.

The battery module may comprise one or more memory elements, the one or more memory elements configured to store one or more battery parameters.

The battery parameters may relate to the battery, or one or more batteries which make up the battery 125 in cases where the battery 125 comprises multiple batteries.

In some configurations, the battery parameters may relate to one or more cells of a battery of the battery.

The battery parameters may comprise:

a) The battery expiry date
b) Battery cell states
c) Battery charge states
d) The number of charge and discharge cycles
e) Battery capacity
f) A voltage of the battery
g) A current output of the battery,
h) A temperature of the battery,
i) Any combination of a)-h).

The apparatus 10 may comprise an electrical socket 114 configured to connect a power cord the apparatus to provide power to the apparatus from a mains power supply.

The power cord removably connects to the electrical socket 114, such that if the power cord becomes damaged during use it can be replaced without having to perform any rewiring of the apparatus 10.

The apparatus 10 may comprise a power cord retainer 351 as shown in FIG. 3. The power cord retainer 351 may connect to a battery cover 126 of the battery 125 (for example, as a battery module), such that during assembly the power cord would be attached to the apparatus 10 after the battery cover 126, with the power cord retainer 351 being attached last. Alternatively, the power cord retainer 351 could be connected to a different part of the housing 100.

Figure 4:
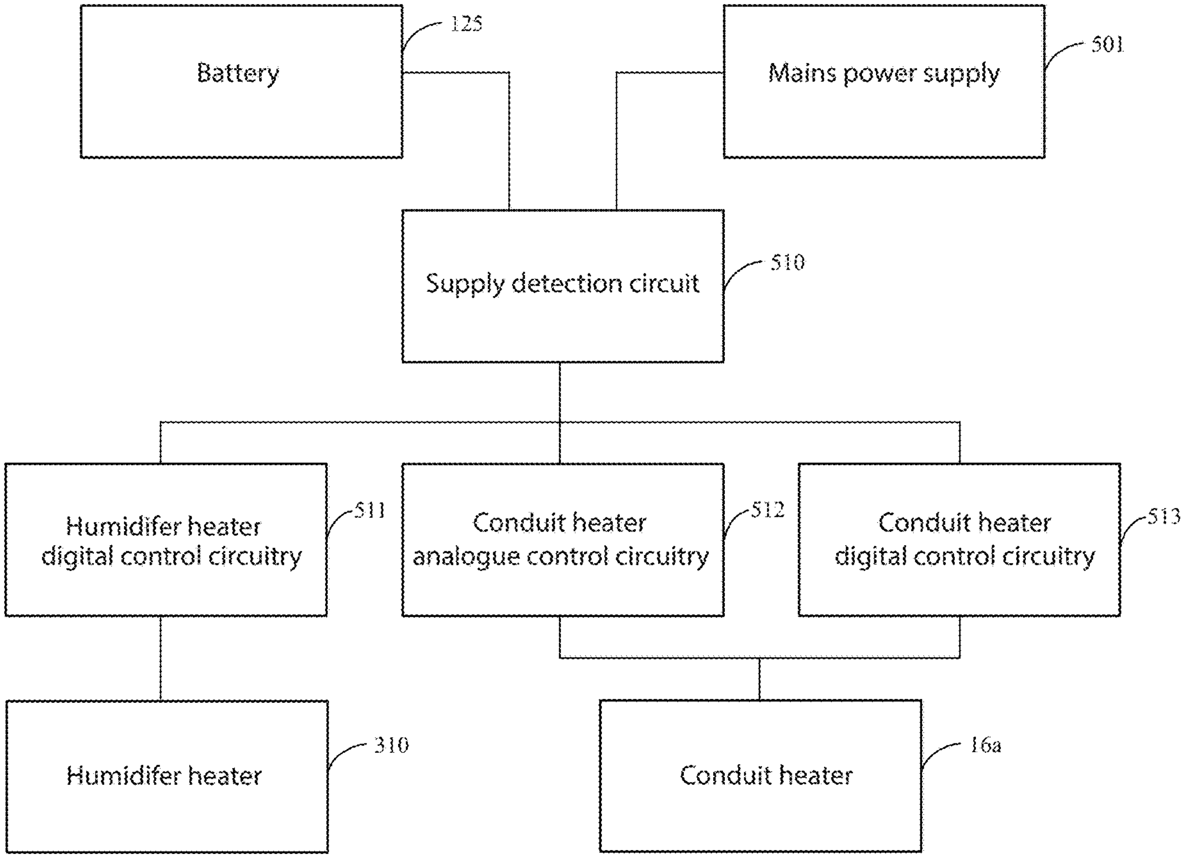
FIG. 4 and FIG. 4A are schematic diagrams of the apparatus including heater control.
Figure 4A:
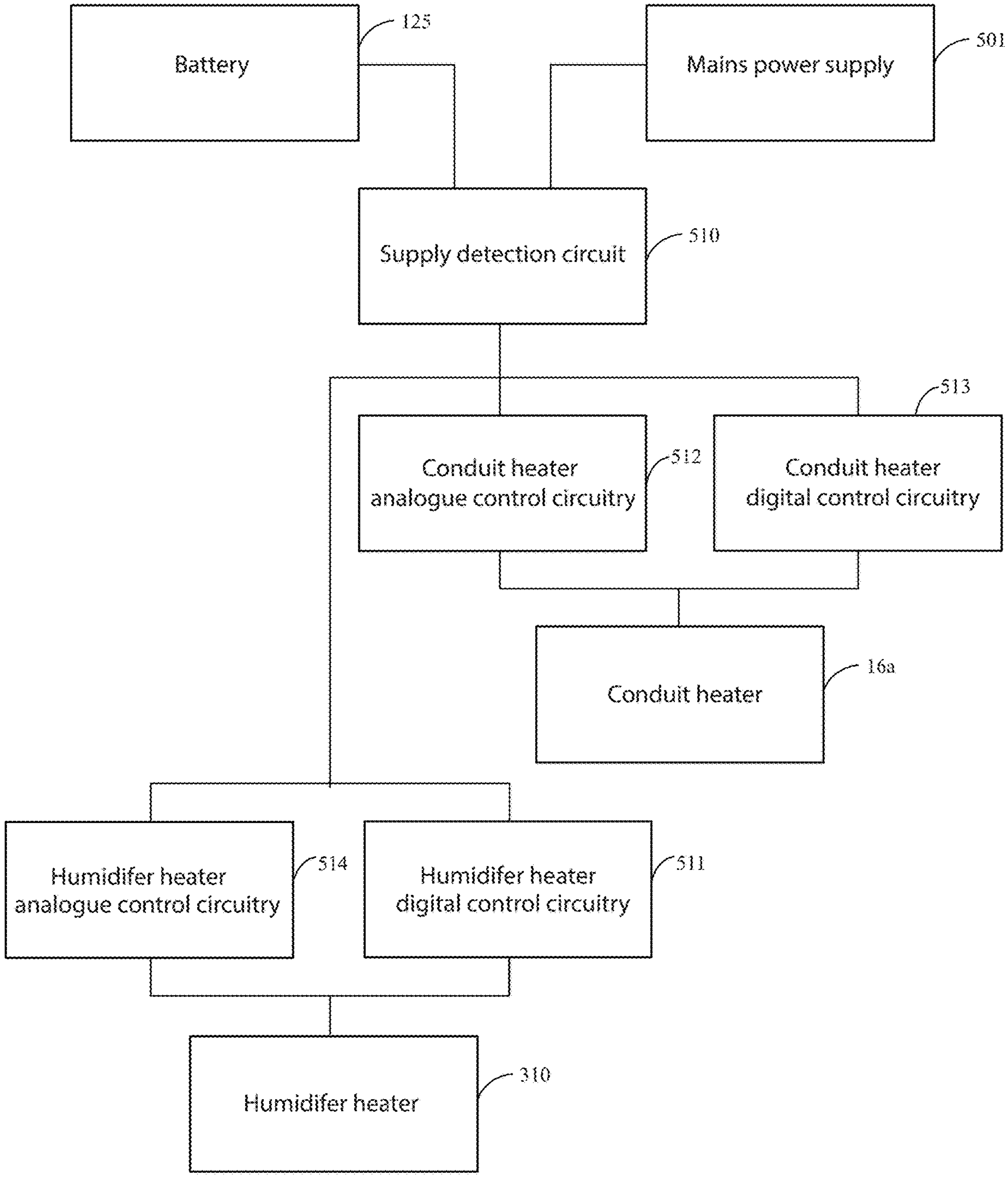

The apparatus may be configured to detect whether the apparatus is operating on the battery or the mains power supply. As shown in FIGS. 4 and 4A, the apparatus 10 may comprise a supply detection circuit 510. The supply detection circuit 510 may comprise one or more of a voltage detection circuits and/or one or more current detection circuits. The supply detection circuit 510 is shown as passing through power from the battery 125 and mains power supply 501, however, it will be appreciated this is a high-level diagram and in some implementations the supply detection circuit 510 may control one or more switches configured to connect the control circuitry to the appropriate power source.

The apparatus 10 may be configured to operate on a battery supply where no mains power supply is detected.

The apparatus may be configured to operate on a battery supply (for example a battery 125) based on an input from a user (optionally via a user interface). In this case the supply detection circuit 510 may only allow the user to select the battery as a power supply if the battery 125 is detected.

The apparatus may comprise a battery charger configured to charge the battery 125. The apparatus may be configured to charge the battery when the apparatus is powered by a mains power supply (and optionally when the voltage of the mains power supply is above a threshold, for example, 110V or 230V) and the battery is not fully charged (and optionally when the battery charge is below a charge threshold, for example, 95%).

The battery module may communicate with the controller 13 one or more battery parameters as described above.

In some configurations, the battery may communicate with the controller 13 to request charging by the battery charger until the battery 125 is fully charged. In some configurations, the battery module comprises a battery monitor which monitors one or battery parameters.

In some configurations, the battery charging and monitoring is performed by circuitry in the battery pack. In some configurations, the battery charging and monitoring is performed by circuitry in the apparatus.

The apparatus 10 may comprise a supply rail configured to provide power to the apparatus.

The apparatus 10 may comprise a mains power supply conversion circuit.

Figure 5:
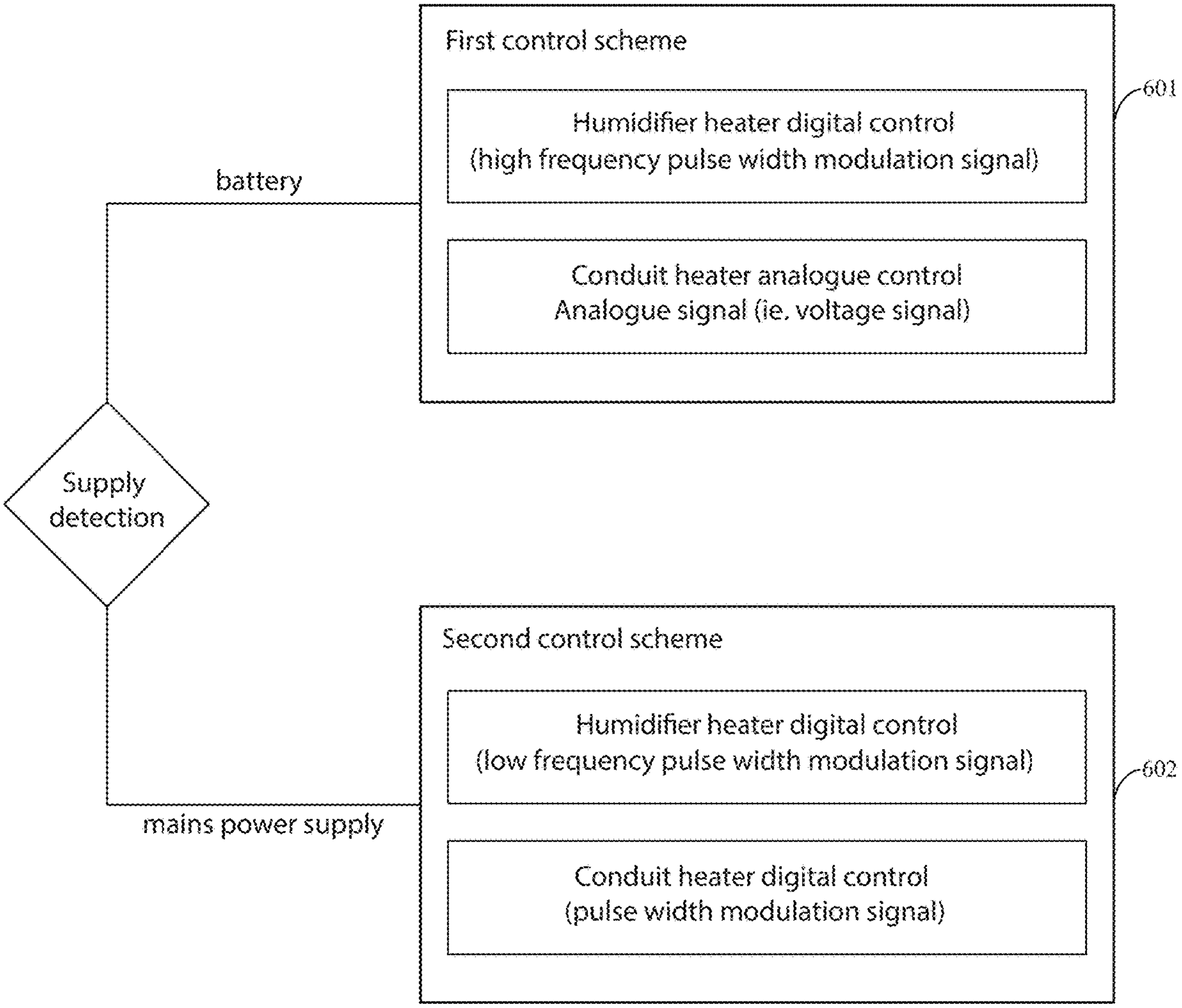
FIGS. 5 and 5A are schematic diagrams of control of the humidifier heater and the conduit heater.
Figure 5A:
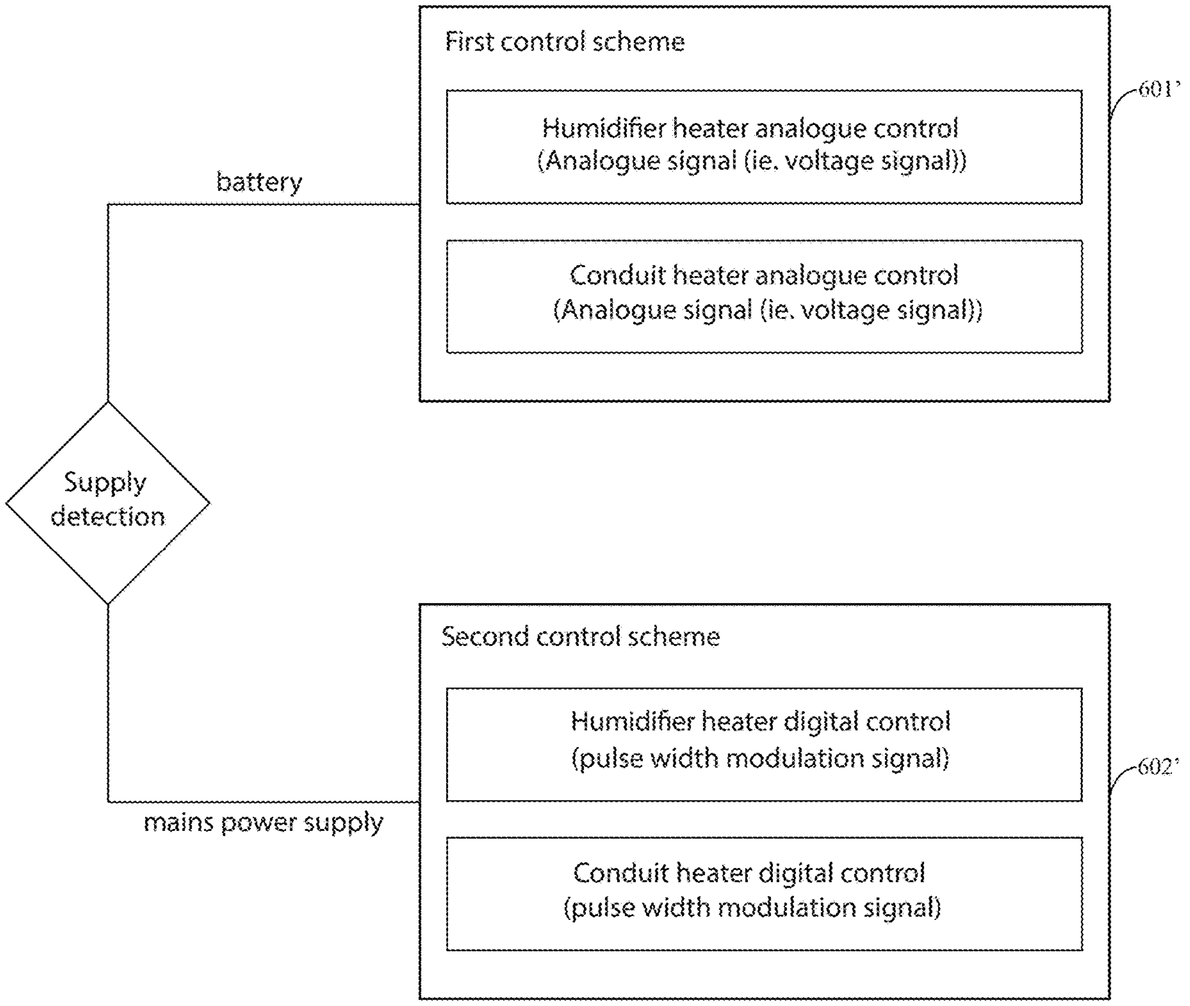
Figure 5B:
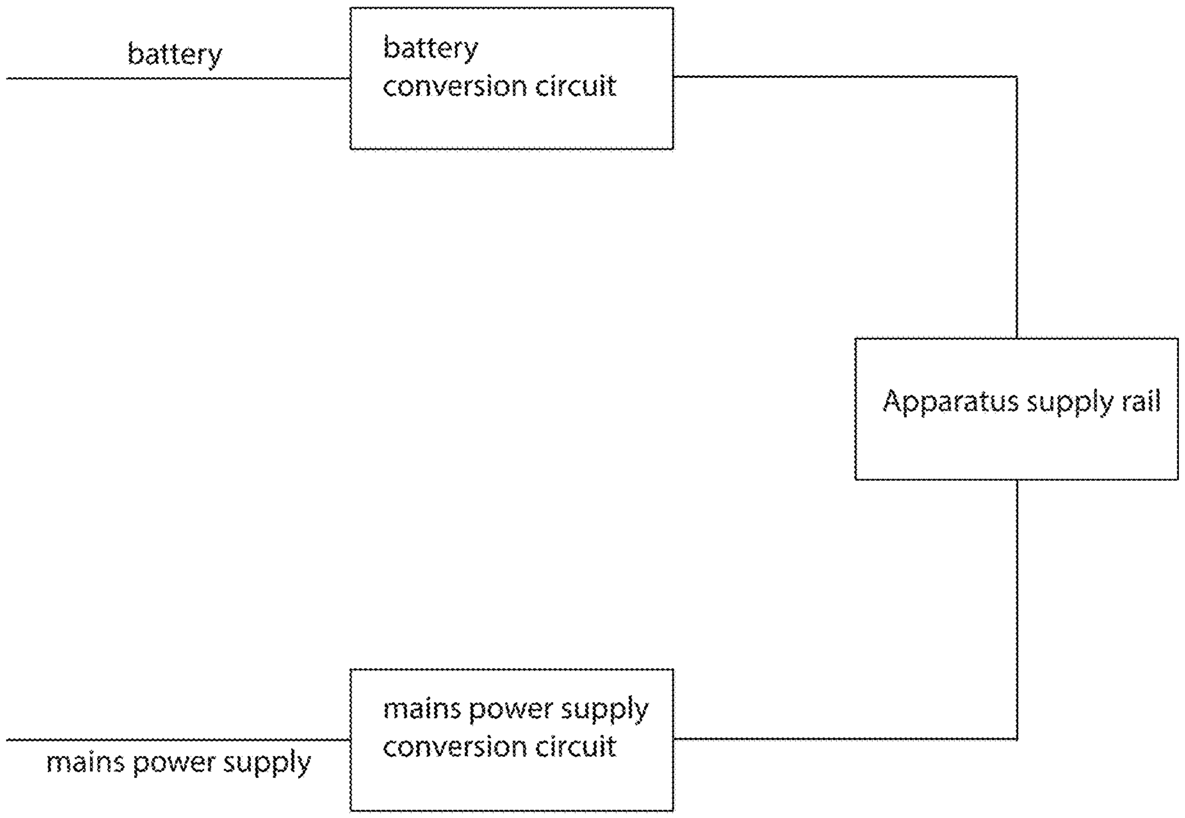
FIG. 5B is a schematic diagram showing the conversion circuits of the apparatus.

The mains power supply conversion circuit may be configured to convert the mains power supply to the supply rail power (for example a supply rail voltage) to power the apparatus as for example as shown in FIG. 5B.

In some configurations, the apparatus, or at least some components of the apparatus may be directly powered by the mains power supply.

The mains power supply conversion circuitry may comprise one or more switched-mode power supplies (or, for example, any other AC to DC converters).

The mains power supply conversion circuit may be configured to convert the mains power supply to a low DC voltage (optionally about 3 Volts DC to about 60 Volts DC).

The apparatus 10 may comprise a battery conversion circuit.

The battery conversion circuit may be configured to convert an output of the battery to a supply rail (for example a supply rail voltage) to power the apparatus, as for example as shown in FIG. 5B.

The battery conversion circuit may be configured to convert the battery to a low DC voltage (optionally about 3 Volts DC to about 60 Volts DC).

The battery conversion circuit may be configured to increase or decrease the battery output voltage, depending on the characteristics of the battery and the components of the apparatus.

The battery conversion circuit may comprise a DC-DC converter.

In some configurations the battery conversion circuit may comprise:

a) A step-down converter
b) A DC-DC converter
c) A step-up converter
d) A boost converter
e) A half bridge converter
f) A flyback converter
g) A push-pull converter
h) A switching converter
i) A switching regulator
j) A linear regulator
k) A linear converter
l) A buck converter
m) A transformer
n) Any combination of a)-m)

The mains power supply conversion circuit and/or battery conversion circuit may provide the apparatus and/or one or more components of the apparatus with power, depending on which power supply the apparatus is using.

In some configurations, the digital control circuitry and analog control circuitry provide power to the heater(s) from the supply rail.

As shown for example in FIG. 2, the oxygen inlet port 28 includes a valve 1003 through which a pressurized gas may enter the respiratory therapy apparatus 10. The valve can control a flow of oxygen into the respiratory therapy apparatus 10. The valve can be any type of valve, including a proportional valve or a binary valve.

The source of oxygen can be an oxygen tank or a hospital oxygen supply. Medical grade oxygen is typically between 95% and 100% purity. Oxygen sources of lower purity can also be used. Examples of valve modules and filters are disclosed in U.S. Provisional Application No. 62/409,543, titled "Valve Modules and Filter", filed on Oct. 18, 2016, and U.S. Provisional Application No. 62/488,841, titled "Valve Modules and Filter", filed on Apr. 23, 2017, which are hereby incorporated by reference in their entireties.

The breathing assistance apparatus 10 can measure and control the oxygen content of the gas being delivered to the patient, and therefore the oxygen content of the gas inspired by the patient.

The breathing assistance apparatus 10 may provide high flow therapy, in which the high flow rate of gas delivered meets or exceeds the peak inspiratory demand of the patient.

Operation sensors 3*a*, 3*b*, 3*c*, such as flow, temperature, humidity, and/or pressure sensors can be placed in various locations in the breathing assistance apparatus 10. Additional sensors (for example, sensors 20, 25) may be placed in various locations on the breathing conduit 16 and/or patient interface 17 (for example, there may be a temperature sensor 29 at or near the end of the inspiratory tube).

The respiratory therapy apparatus 10 may have a communications module 15 to enable the controller 13 to receive signals 8 from the sensors and/or to control the various components of the breathing assistance apparatus 10, including but not limited to the flow generator 11, humidifier 12, heater 16*a*, humidifier heater, or accessories or peripherals associated with the breathing assistance apparatus 10. Additionally, or alternatively, the communications module 15 may deliver data to a remote server or enable remote control of the respiratory therapy apparatus 10 or respiratory therapy system 1.

The communications module may comprise a transmitter, receiver and/or transceiver.

The communications module 15 may act as a network interface (for example, as a modem).

The communications module 15 may use one or more communication protocols known in the art, for example, Wi-Fi, Bluetooth, Zigbee, cellular (3G, 4G, or 5G, etc).

The communications module 15 may allow for communication between the apparatus and a mobile device (for example, a phone or a tablet via Bluetooth or Wi-Fi)

The communications module may comprise a number of separate transmitters, receivers and/or transceiver for each, or for a group of communication protocol(s).

The communications module 15 may be configured to transmit data and receive data from one or more devices (for example, a server) as described in more detail below.

In some configurations, one or more leak or blockage events, or alarms (as described in more detail below) may be transmitted to one or more servers and/or devices (for example, a computer, phone or tablet). Additional information (for example, the time, duration, or severity) associated with the event or alarm may be additionally transmitted to the server and/or device.

As described above, the breathing assistance apparatus 10 can measure and control the oxygen content of the gas being delivered to the patient. Oxygen may be measured by placing one or more gas composition sensors (such as an ultrasonic transducer system) after the oxygen and ambient air have been mixed. The measurement can be taken within the respiratory therapy apparatus 10, the patient breathing conduit 16, the patient interface 17, or at any other suitable location.

The oxygen concentration measured in the apparatus may be equivalent to the fraction of delivered oxygen (FdO2) and may be substantially the same as the oxygen concentration the patient is breathing, the fraction of inspired oxygen (FiO2), and as such the terms may be seen as equivalent.

Oxygen concentration may also be measured by using flow rate sensors on at least two of the ambient air inlet conduit, the oxygen inlet conduit, and the patient breathing conduit to determine the flow rate of at least two gases. By determining the flow rate of both inlet gases or one inlet gas and one total flow rate, along with the assumed or measured oxygen concentrations of the inlet gases (about 20.9% for ambient air, about 100% for oxygen), the oxygen concentration of the final gas composition can be calculated. Alternatively, flow rate sensors can be placed at all three of the ambient air inlet conduit, the oxygen inlet conduit, and the breathing conduit to allow for redundancy and testing that each sensor is working correctly by checking for consistency of readings. Other methods of measuring the oxygen concentration delivered by the breathing assistance apparatus 10 can also be used.

The breathing assistance apparatus 10 can include a patient sensor 26, such as a pulse oximeter or a patient monitoring system, to measure one or more physiological parameters of the patient, such as a patient's blood oxygen concentration (for example, blood oxygen saturation (SpO2)), heart rate, respiratory rate, perfusion index, and provide a measure of signal quality. The sensor 26 can communicate with the controller 13 through a wired connection or by communication through a wireless transmitter on the sensor 26. The sensor 26 may be a disposable adhesive sensor designed to be connected to a patient's finger. The sensor 26 may be a non-disposable sensor (i.e., a re-useable sensor). Sensors that are designed for different age groups and to be connected to different locations on the patient are available and can be used with the breathing assistance system 1. The pulse oximeter can be attached to the patient, typically at their finger, although other places such as an earlobe are also an option. The pulse oximeter can be connected to a processor in the respiratory therapy apparatus 10 and can constantly provide signals indicative of the patient's blood oxygen saturation. The patient sensor 26 can be a hot-swappable device, which can be attached or interchanged during operation of the breathing assistance apparatus 10. For example, the patient sensor 26 may connect to the breathing assistance apparatus 10 using a USB interface or using wireless communication protocols (such as Bluetooth®).

When the patient sensor 26 is disconnected during operation, the breathing assistance apparatus 10 may continue to operate in its previous state of operation for a defined time period. After the defined time period, the breathing assistance apparatus 10 may trigger an alarm, transition from automatic mode to manual mode, and/or exit control mode (e.g., automatic mode or manual mode) entirely. The patient sensor 26 may be a bedside monitoring system or other patient monitoring system that communicates with the breathing assistance apparatus 10 through a physical or wireless interface.

The breathing assistance apparatus 10 may comprise or be in the form of a high flow therapy apparatus.

High flow therapy as discussed herein is intended to be given its typical ordinary meaning as understood by a person of skill in the art which generally refers to a breathing assistance apparatus delivering a targeted flow of humidified respiratory gases via an intentionally unsealed patient interface with flow rates generally intended to meet or exceed inspiratory flow of a patient. Typical patient interfaces include, but are not limited to, a nasal or tracheal patient interface. Typical flow rates for adults often range from, but are not limited to, about fifteen litres per minute to about sixty litres per minute or greater. Typical flow rates for paediatric patients (such as neonates, infants and children) often range from, but are not limited to, about one litre per minute per kilogram of patient weight to about three litres per minute per kilogram of patient weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names.

For example, in some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient, 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may, in some configurations, deliver gases to the patient at a flow rate of between about 1 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy may be effective in meeting or exceeding the patient's inspiratory flow, increasing oxygenation of the patient, and/or reducing the work of breathing.

High flow therapy may be administered to the nares of a patient and/or orally, or via a tracheostomy interface.

High flow therapy may generate a flushing effect in the nasopharynx such that the anatomical dead space of the upper airways is flushed by the high incoming gases flow. This can create a reservoir of fresh gas available for each and every breath, while reducing re-breathing of nitrogen and carbon dioxide. Meeting inspiratory demand and flushing the airways is additionally important when trying to control the patient's FdO2. High flow therapy can be delivered with a non-sealing patient interface such as, for example, a nasal cannula. High flow therapy may slow down respiratory rate of the patient. High flow therapy may provide expiratory resistance to a patient.

High flow therapy may be used to treat patients with obstructive pulmonary conditions e.g., COPD, bronchiectasis, dyspnea, cystic fibrosis, emphysema and/or patients with respiratory distress or hypercapnic patients.

The term "non-sealing patient interface" (i.e., unsealed patient interface) as used herein can refer to an interface providing a pneumatic link between an airway of a patient and a gases flow source (such as from flow generator 11) that does not completely occlude the airway of the patient. A non-sealed pneumatic link can comprise an occlusion of less than about 95% of the airway of the patient. The non-sealed pneumatic link can comprise an occlusion of less than about 90% of the airway of the patient. The non-sealed pneumatic link can comprise an occlusion of between about 40% and about 80% of the airway of the patient. The airway can include one or both nares of the patient and/or their mouth. For a nasal cannula the airway is through the nares.

In some configurations, the "non-sealing patient interface" may comprise a tracheal interface.

CPAP therapy may comprise providing gases to a user at a continuous positive pressure (and optionally one or more therapy parameters as described in more detail above.)

BCPAP therapy may comprise providing gases to a user at a therapy flow rate (and optionally one or more therapy parameters as described in more detail above.)

Bilevel therapy may comprise providing gases to a user at a therapy IPAP and EPAP (and optionally one or more therapy parameters as described in more detail above.)

A sealed interface, may be used when the apparatus is provided CPAP, Bilevel or BCPAP therapy, The flow generator 11 can be or comprises a blower module. The blower module may comprise at least one blower 11 configured to generate said flow of gases.

The flow generator 11 can include an ambient air inlet port 27 through which ambient room air can be entrained into the blower. The breathing assistance apparatus 10 may also include an oxygen inlet port 28 leading to a valve through which a pressurized gas may enter the flow generator 11. The valve can control a flow of oxygen into the flow generator 11. The valve can be any type of valve, including a proportional valve or a binary valve.

The blower 11 can operate at a motor speed of greater than about 1,000 RPM and less than about 8,000 RPM, greater than about 2,000 RPM and less than about 10,000 RPM, or between any of the foregoing values. The blower 11 can mix the gases entering the blower 11 through the gas inlet (for example, the ambient air inlet port 27 and/or an oxygen inlet port 28). Using the blower 11 as the mixer can decrease the pressure drop relative to systems with separate mixers, such as static mixers comprising baffles.

The breathing assistance apparatus may further comprise a gas composition sensor. The gas composition sensor may be the sensor described below (for example the ultrasonic transducer configuration).

The breathing assistance apparatus 10 comprises a flow sensor. The flow sensor may be configured to measure a flow rate of the flow of breathable gas to a patient.

The controller 13 may comprise one or more processors. The processors may be configured with computer-readable instructions.

The controller 13 may comprise at least one memory element. The memory element may be configured to store said computer-readable instructions.

The memory element may be non-transitory computer readable medium.

The controller 13 may be a microprocessor or an ASIC, FPGA or a combination of ICs or microprocessors or other suitable components and/or architectures.

The breathing assistance apparatus may comprise at least one display module, configured to display an alarm output.

The breathing assistance apparatus may comprise at least one audible module configured to emit an audible alarm.

In some configurations the at least one audible module may comprise a speaker.

The display module may comprise at least one display (for example, a liquid crystal display (LCD), or a light emitting diode (LED) display, although it will be appreciated any display technology may be used).

The display module may be configured to receive inputs to the system (for, example as a touch screen) and therefore be at least part of, or display part of the user interface 14.

The display module may be configured to be an input/output (I/O) module. For example, the display module may be configured to receive inputs from a user and provide outputs to a user (for example as part of, or to display part of the user interface 14).

The display module may communicate with the controller 13. In some configurations the display module may provide information to the controller 13 (for example set points). In some configurations the display module may receive information from the controller 13 (for example alarms, sensor outputs, and/or other calculated variables.)

Some examples of flow therapy apparatuses are disclosed in International Application No. PCT/NZ2016/050193, titled "Flow Path Sensing for Flow Therapy Apparatus", filed on Dec. 2, 2016, and International Application No. PCT/IB2016/053761, titled "Breathing Assistance Apparatus", filed on Jun. 24, 2016, which are hereby incorporated by reference in their entireties.

As shown for example in FIG. 2, the breathing assistance apparatus comprises a housing 100. The housing 100 has a housing upper chassis 102 and a housing lower chassis 202. However, it will be appreciated that in some configurations, the housing may have a number of components.

Figure 6:
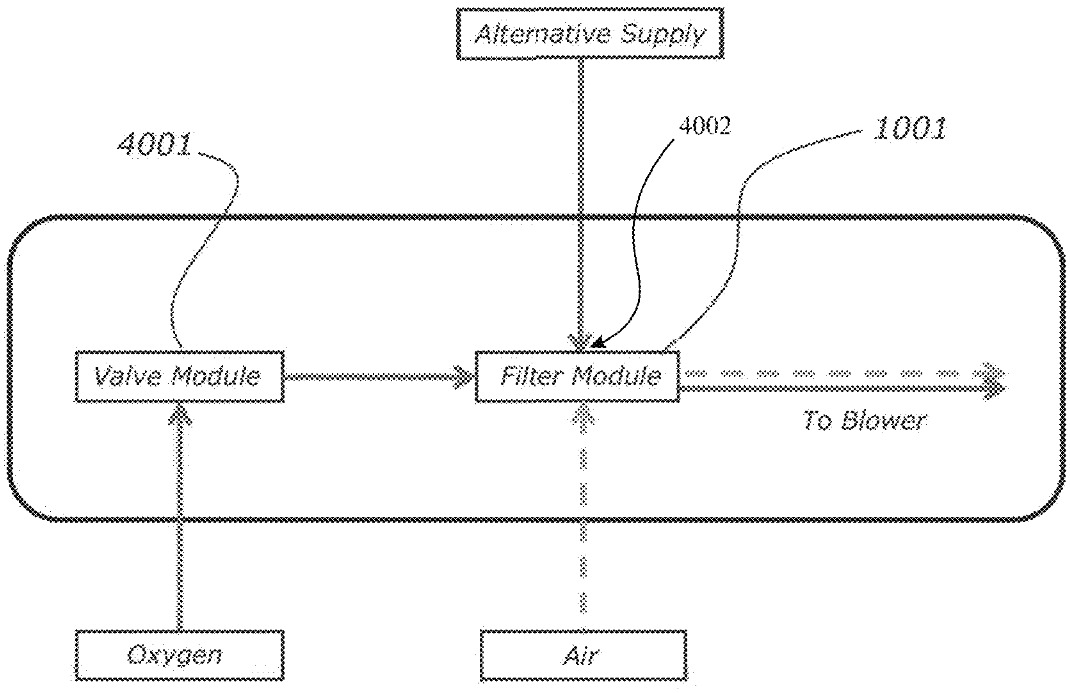
FIG. 6 is a schematic gas flow path diagram for the filter module and the valve module, with the solid line arrows representing the flow of gases.

For example, as shown in FIG. 6, the apparatus 10 may comprise a valve module that controls the flow of oxygen and/or other gases entering the gas flow path of the apparatus 10 and enables the apparatus 10 to regulate the proportion of oxygen entrained in the airflow. The valve module is formed as a modular unit for ease of manufacture, assembly, servicing, or replacement. For example, in the event of malfunction, routine maintenance, or future upgrade/improvement.

The valve module may be configured to operate to control the oxygen concentration of the gases provided to the user to at a therapy oxygen concentration.

The apparatus 10 may comprise a filter module 1001, which may comprise a filter.

The filter modules and valve modules described herein may provide varying gas flow paths for the apparatus. For example, the valve module may control the flow of oxygen entering the gas flow path of the apparatus, via the valve module and filter module. Alternatively, the valve module may be bypassed by means of direct connection of an alternative oxygen source to the filter module via an alternative supply inlet. This may be practical in circumstances where a user may wish to manually adjust the oxygen supply (i.e., by a wall-supply rotameter).

It will be appreciated that the filter modules and the valve modules described herein may be used separately in apparatuses for delivering a flow of gas. Alternatively, the filter and the valve module may be used together as a filter and valve assembly for improved functionality.

In the configurations shown, the apparatus 10 receives oxygen by at least one of the following:

- via the valve module (for automatic oxygen regulation by the apparatus), or
- via the alternative gases inlet provided on the top of the filter (allowing attachment of a manually adjustable oxygen supply—such as a wall supply regulated by a regulator).

In some configurations, the alternative gases inlet may be provided with a therapeutic gas that is not oxygen (for example, heliox)

The apparatus 10 may comprise a manifold. The manifold may be located on the housing. The manifold may provide one or more of: the oxygen inlet, the alternative gases inlet, and/or the air inlet.

The manifold may provide the oxygen, alternative gases, and/or ambient air to the valve module, filter module, and/or the blower.

The manifold may be provided upstream of the blower.

The oxygen inlet or alternative gasses supply inlet may be provided on a side of the manifold.

The manifold may allow excess oxygen to overflow to the ambient environment, and/or may allow oxygen to overflow to the ambient environment if the blower is off and oxygen is continually supplied. This prevents accumulation of O2 in the housing.

The manifold may comprise one or more baffles that help to mix the oxygen and/or the alternative gases and air.

The manifold may also comprise a filter configured to filter the oxygen and/or the alternative gases and/or air from the respective inlets.

The various configurations described are exemplary configurations only. Any one or more features from any of the configurations may be used in combination with any one or more features from any of the other configurations.

In some configurations, a motor and/or a sensor sub-assembly (for example containing one or more sensors) may be located in the housing.

The motor and/or sensor sub-assembly may be located recess on in the underside of the housing. The recess may alternatively be in the rear, side, front, or top of the housing. The air and/or oxygen inlets may also be positioned differently as required.

As another example, rather than the humidification chamber and chamber bay being configured so that the humidification chamber is inserted into and removed from the chamber bay from a front of the housing, the configuration could be such that the humidification chamber is inserted into and removed from the chamber bay from a side, rear, or top of the housing.

As another example, while the filter modules are described as being inserted into the housing from above and the valve modules inserted into the housing from below, either or both of those components could be inserted into any suitable part of the housing, such as an upper part, lower part, side part, front part, or rear part.

The filter module and valve module are described with reference to a breathing assistance apparatus that can deliver heated and humidified gases to a patient or user.

The filter module and/or valve module may alternatively be used with an apparatus that does not require a humidifier and therefore does not require the humidification chamber 300. For example, it will be appreciated that the configuration that isolates the motor and gas flow path from the electrical and electronic components has broad applications in other types of gas delivery apparatuses.

As described above the apparatus is configured to be powered by a battery or a mains power supply (for example as shown as FIG. 4 and FIG. 4A).

The controller 13 may be configured to control the heater of the humidifier and/or the heater of the conduit according to a first control scheme and a second control scheme.

In some configurations, the controller 13 may transmit commands to humidifier heater sub-controller and/or the conduit heater sub-controller.

In some configurations, the first control scheme is a first power control scheme.

In some configurations, the second control scheme is a second power control scheme.

When the apparatus is powered by the battery 125, the controller is configured to control the heater of humidifier and/or the heater of the conduit according to a first control scheme.

In some configurations, when the apparatus is powered by a peak power limited supply, the controller is configured to control the heater of humidifier and/or the heater of the conduit according to a first control scheme.

In some configurations, when the apparatus is powered by an integrated supply, the controller is configured to control the heater of humidifier and/or the heater of the conduit according to a first control scheme.

The control schemes described below refer to both the heater of the conduit and the heater of the humidifier however it will be appreciated that they may equally be applied to only one of the heaters (and not both as described below).

The first control scheme may comprise controlling the heater of the humidifier by digital control (for example, digital power control) for example as shown in FIG. 5.

Additionally, or alternatively, the first control scheme may comprise controlling the heater of the conduit by analog control (for example, analog power control) for example, as shown in FIG. 5.

In some configurations, the first control scheme may comprise controlling the heater of the humidifier by analog control (for example, analog power control) for example, as shown in FIG. 5A.

When the apparatus is powered by the mains power supply, the controller is configured to control the heater of humidifier and/or the heater of the conduit according to a second control scheme.

In some configurations, when the apparatus is powered by a non-peak power limited supply, the controller is configured to control the heater of humidifier and/or the heater of the conduit according to a second control scheme.

In some configurations, when the apparatus is powered by an external supply, the controller is configured to control the heater of the humidifier and/or the heater of the conduit according to a second control scheme.

The second control scheme may comprise controlling the heater of the humidifier by digital control.

Additionally, or alternatively, the second control scheme may comprise controlling the heater of the conduit by digital control.

The first control scheme may comprise providing the heater of the humidifier with a high frequency pulse-width modulation signal.

The second control scheme may comprise providing the heater of the humidifier with a low frequency pulse-width modulation signal.

The frequency of the high frequency pulse-width modulation signal is a greater than the frequency of the low frequency pulse-width modulation signal.

FIG. 5 shows an example of the first control scheme 601 and second control scheme 602 being used to control the heater of the humidifier and heater of the conduit based on whether the apparatus is operating on a battery 125 or a mains power supply.

The first control scheme 601 comprises controlling the humidifier heater by digital control by providing a high frequency pulse-width modulation signal. The first control scheme 601 further comprises controlling the conduit heater by analog control by providing an analog control signal (for example, a voltage signal).

The second control scheme 602 comprises controlling the humidifier heater by digital control by providing a low frequency pulse-width modulation signal. The second control scheme 602 further comprises controlling the conduit heater by digital control by providing a pulse-width modulation signal (optionally, a low frequency pulse-width modulation signal as described elsewhere).

FIG. 5A shows an alternative example of the first control scheme 601' and second control scheme 602' being used to control the heater of the humidifier and heater of the conduit based on whether the apparatus is operating on a battery 125) or a mains power supply.

The first control scheme 601' comprises controlling the humidifier heater by analog control by providing an analog control signal. The first control scheme 601' further comprises controlling the conduit heater by analog control by providing an analog control signal (for example, a voltage signal).

The second control scheme 602 comprises controlling the humidifier heater by digital control by providing a pulse-width modulation signal (optionally, a low frequency pulse-width modulation signal). The second control scheme 602 further comprises controlling the conduit heater by digital control by providing a pulse-width modulation signal (optionally, a low frequency pulse-width modulation signal as described elsewhere).

Figure 8:
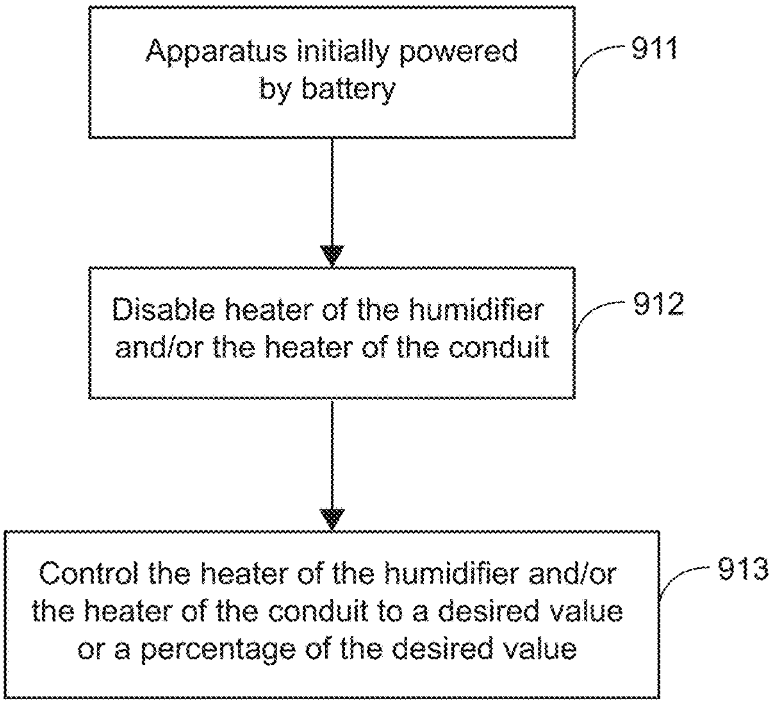
FIGS. 8 and 9 show schematic diagrams of control of the apparatus when initially powered by a battery.

In some configurations, when the apparatus is initially powered by a power limited supply i.e. a battery—as shown in step 911 of FIG. 8, (for example when entering a first control scheme 601, 601') the apparatus may be configured to disable the humidifier heater and/or the conduit heater as shown in step 912 of FIG. 8.

Disabling the humidifier heater and/or the conduit may comprise one or more of: disabling the control circuitry (for example the analog control circuitry and/or the digital control circuitry) and/or providing an off control signal.

The apparatus being initially powered by a power limited supply may be when the apparatus switches to a battery, for example when the mains power supply is removed.

The apparatus may then (optionally after a predetermined amount of time) control the humidifier heater and/or the conduit heater to the desired value (for example a desired power, or to reach a desired therapy parameter) or a percentage of a desired value as shown in step 913 of FIG. 8. The apparatus may (control the humidifier heater and/or the conduit heater example increasing a control signal to a desired value by increasing a control signal for example a digital control signal or an analog control signal. This may prevent the peak rating(s) of the battery being exceed by activation of the heaters.

The apparatus may control the control the humidifier heater and/or the conduit heater to the desired value or a percentage of a desired value at, or below a predetermined rate.

Figure 9:
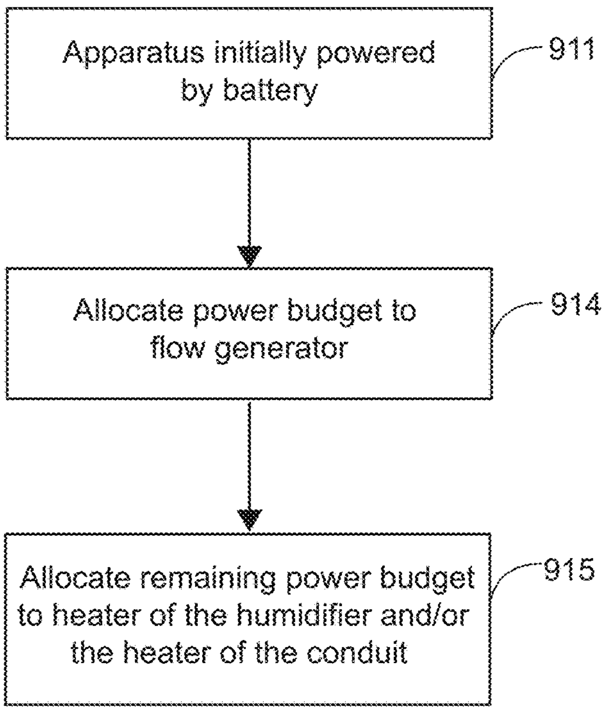

In some configurations, when the apparatus is powered by a power limited supply i.e. a battery (for example when entering a first control scheme 601, 601')—as shown in step 911 of FIG. 9, the apparatus may be configured to prioritise delivery power to the flow generator (or optionally a blower of the flow generator) over the humidifier heater and/or the conduit heater. The battery power rating may set a power budget which may be allocated to the flow generator, the humidifier heater and the conduit heater. The power budget may be allocated to the flow generator—as shown in step 914 of FIG. 8 in preference to the humidifier heater and/or the conduit heater.

For example, if the power rating of the battery is 100 W, and the combined desired power of the blower, the humidifier heater and the conduit heater is greater than 100 W, then the blower will be allocated power in priority to the humidifier heater and/or the conduit heater.

In some configurations, the power delivered to the humidifier heater and/or the conduit heater will be based on a power remaining from the power budget—as shown in step 915 of FIG. 8. The power remaining from the power budget may be the power budget less the power required to power the flow generator (for example to a therapy flow rate and/or a therapy pressure). If the power remaining is greater than the combined desired power of the humidifier heater and/or the conduit heater, then the apparatus may be configured to reduce the power provided to the humidifier heater and/or the conduit heater (optionally to the remaining power budget)

For example, if the remaining power budget is 60 W, and the desired power is greater than 60 W, then the power delivered to the humidifier heater and/or the conduit heater may be reduced to 60 W.

In some configurations, when the apparatus is powered by a power limited supply i.e. a battery (for example when entering a first control scheme 601, 601') the apparatus may be configured to disable the humidifier heater and/or the conduit heater (for example by providing no control signal and/or a zero control signal) when the battery charge reaches a threshold. In some configurations, the threshold is about 5% to about 40%, or about 10% to about 30% or about 20%.

Digital control may comprise generating a signal that has an ON state and an OFF state. The OFF state signal level may be ground (or 0 volts) and the ON state signal level may be the supply voltage (for example, the supply voltage from one or more battery conversion circuit and/or the mains power supply conversion circuit as described in more detail above, and/or voltage from one or more voltage conversion circuits). The signal may then be provided to the heater to control the heater.

The ON state may be, for example, any suitable positive or negative voltage.

The magnitude of the ON state voltage can be selected based on the desired range of power demand(s) expected, electrical characteristics of the heater, and/or the maximum allowable to PWM frequency to stay within EMI requirements. It will be appreciated that various different apparatuses may have different supply voltages and may step up or step down the supply voltages for powering the heating components—in this case the ON state may be based on the stepped up or stepped down voltage.

Figure 7A:
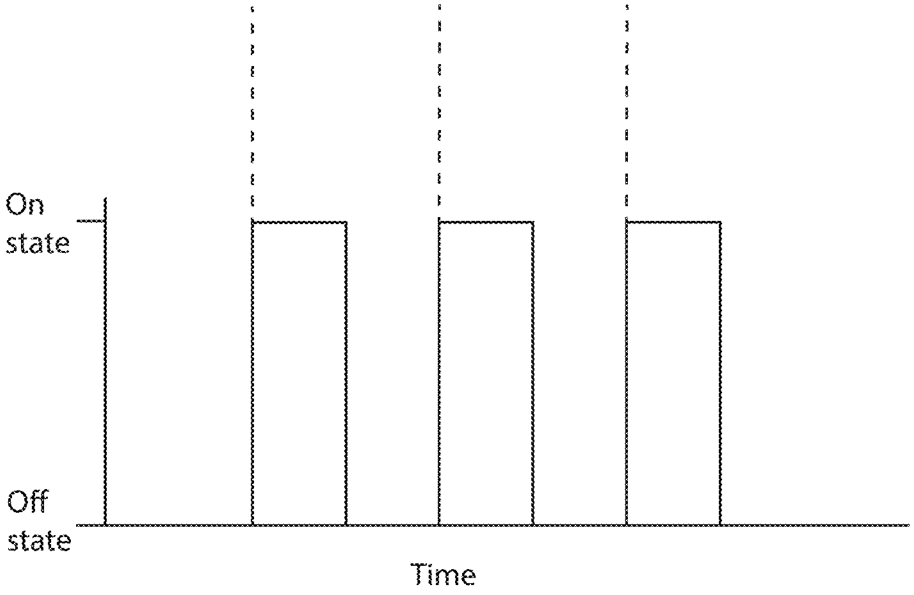
FIGS. 7A and 7B show examples of pulse-width modulation signals.
Figure 7B:
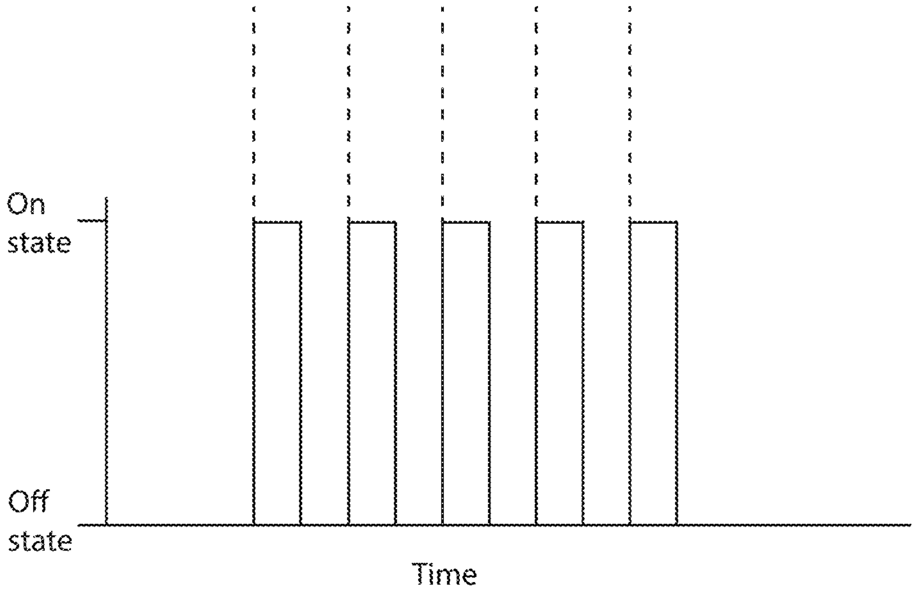

Digital control may comprise, for example, pulse-width modulation (for example, as shown in FIGS. 7A and 7B). However, it will be appreciated that in some configurations digital control may comprise pulse-density-modulation (PDM), and pulse-frequency modulation (PFM).

Analog control may be providing an analog control signal (as, for example, a modulated voltage or current signal) to the heater of the conduit and/or to the heater of the humidifier.

Providing an analog control signal may comprise controlling or modulating or regulating an analog signal providing this to a conduit heater. In configurations where the analog signal is a voltage signal, the voltage signal may be provided across the terminals of the heater of the conduit. In configurations where the analog signal is a current signal, the current signal may be supplied to the heater of the conduit.

It will be appreciated that the analog control signal may be generated based on one or more electrical characteristics of the heater(s) and/or the associated circuitry of the heater (s). For example, a voltage signal may be generated based on a resistance and/or a current measured of the heater(s) and/or the associated circuitry of the heater(s).

Analog control may comprise generating a continuous (or near-continuous) control signal, for example, a continuous voltage signal or a continuous current signal.

Analog control may comprise generating a periodic signal or a non-periodic signal. A periodic signal may be smooth (for example, a sinusoidal signal as for example shown in FIG. 7E) or non-smooth (for example, a triangle wave as for example shown in FIG. 7D).

In some configurations, analog power control may comprise generating a sinusoidal wave and/or a modified sinusoidal wave as the analog control signal. The sinusoidal wave and/or a modified sinusoidal wave may be generated based on a desired power to be provided to the heater.

The properties or parameters of the sinusoidal wave and/or modified sinusoidal wave generated may be varied according to the voltage and/or current and/or power requirements for the heaters. For example, the amplitude, magnitude, frequency, and/or a DC offset of the wave(s) can be controlled.

Figure 7C:
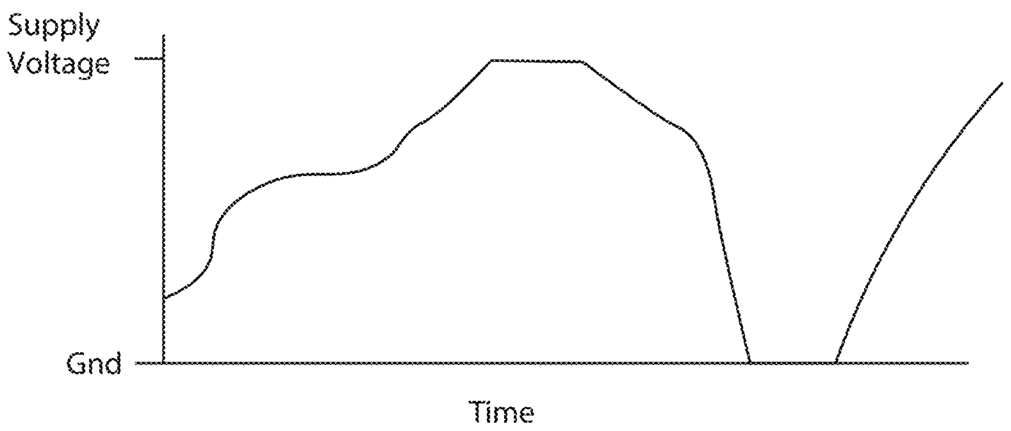
FIG. 7C-7E show examples of a voltage signal as an analog control signal.

The analog control signal may be, for example, a continuous signal which varies between 0 volts and a supply voltage (for example, as shown in FIG. 7C)—as opposed to the digital control signal which may have a discrete value that is either 0 volts or a supply voltage.

FIG. 7C shows an example analog control signal as a voltage signal. As described elsewhere the analog control signal may be controlled by the controller to reach a particular control output (i.e., a specific power delivery and/or a specific therapy parameter) and varies between ground and the supply voltage. In some portions of the signal as shown in FIG. 7C the voltage reaches supply voltage and ground.

Figure 7D:
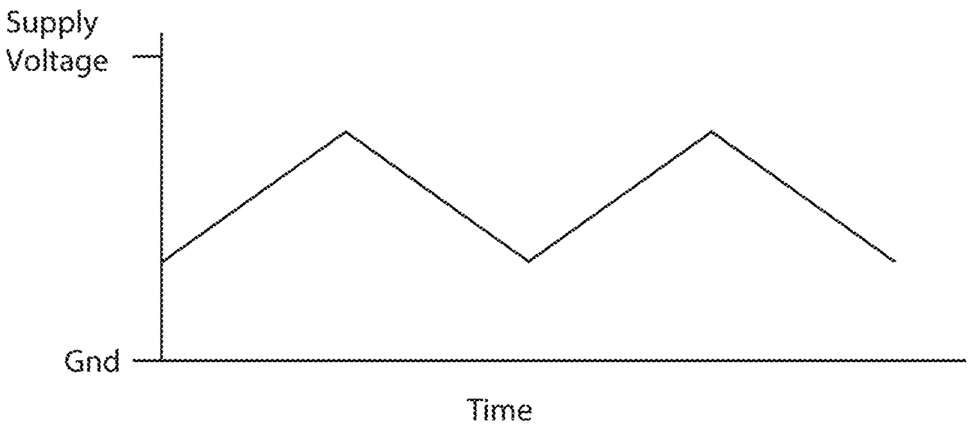

FIG. 7D shows another example analog control signal as a voltage signal. In FIG. 7D the analog control signal is a triangle wave. In some configurations, the triangle wave may be symmetrical or asymmetrical triangle wave. In some configurations the triangle wave may be a sawtooth wave.

Figure 7E:
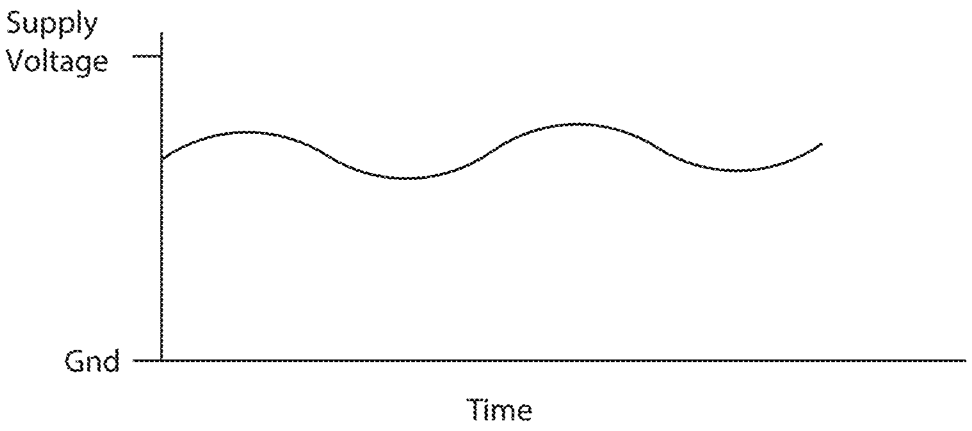

FIG. 7E shows another example analog control signal as a voltage signal. In FIG. 7D the analog control signal is a sinusoidal shape.

The digital control pulse-width modulation signal (for example, the low frequency pulse-width modulation signal and high frequency pulse-width modulation signal) may be a periodic rectangular pulse type signal that switches between ground (i.e., 0 volts) and the supply voltage level (for example, the supply voltage from one or more battery or mains power supply conversion circuits as described in more detail above).

FIGS. 7A and 7B show an example of a low frequency pulse-width modulation signal and high frequency pulse-width modulation signal, respectively, and relative to each other.

The duty cycle of the low frequency pulse-width modulation signal of FIG. 7A is approximately 50% and is the same as the duty cycle of the high frequency pulse-width modulation signal of FIG. 7B. However, the frequency of the low frequency pulse-width modulation signal (of FIG. 7A) is less than the frequency of the high frequency pulse-width modulation signal (of FIG. 7B).

The controller 13 of the apparatus 10 may be configured to control the duty cycle of the pulse-width modulation signal to:

a) control the heater of the humidifier or the heater of the conduit to reach one or more temperatures (for example, a temperature of the humidifier of the heater)
b) control the heater of the humidifier or the heater of the conduit to reach therapy parameters (for example, a therapy humidity level).
c) control the heater of the humidifier or the heater of the conduit to reach one or more desired powers.

It will be appreciated that the control output in all these cases could be power (i.e., 0-100% duty cycle).

As described above, control of the heaters of the apparatus may be by digital control or analog control.

Examples of Control Methodologies for the Heater of the Conduit and/or the Heater of the Humidifier:

| | |
|---|---|
| Digital control | Pulse width modulation (for example, low frequency pulse width modulation or high frequency pulse width modulation) |
| Analog control | Voltage Modulation |
| | Current Modulation |
| | Resistance Modulation |

Each of the control methodologies as described above may have particular advantages and disadvantages for particular heaters and particular apparatuses.

For example, as described above—high frequency pulse width modulation may generate more EMI as compared to low frequency pulse width modulation or analog control (in particular when used to power the heater of the conduit).

However, high frequency pulse width modulation may have a lower peak power requirement when compared to low frequency pulse width modulation, in particular when paired with suitable energy storage (for example capacitive energy storage).

Given high frequency pulse width modulation does not have the same negative EMI effect when used to power the heater of the humidifier (as there is minimal antenna effect) and has a lower peak power requirement, high frequency pulse width modulation may be beneficial for use in controlling the heater of the humidifier in certain scenarios (for example, when powered by a peak power limited supply—i.e., a battery).

With respect to analog control—analog control may generate less EMI than digital control.

However, in analog control, the control circuitry required to generate the desired analog signal is generally more expensive and complex than digital control circuitry, as it typically requires more electrical and/or electronic components. Because analog control does not have a digital control signal varying between a full ON state and a full OFF state, the transient peak power draws in analog control are generally less than in digital control, as in analog control the power supply does not need to provide the sudden rush of current associated with the transition from the OFF state to the ON state in digital control. Analog control may also provide for a more consistent signal with a lower rate of change of a delivered power, as compared to digital control where during switching the rate of change of delivered power is much higher which may cause the peak power drawn on the power supply to be larger.

Various analog control methods are disclosed. Analog control by voltage modulation may be by providing a voltage signal to the heater. Analog control by current modulation may be by providing a current signal to the heater. Analog control by resistance modulation may be by varying a resistance of a component in a circuit with a voltage supply and the heater to indirectly control the power delivered to the heater. In some configurations, the component may be, for example, a digital potentiometer (or another electronically controllable resistive component).

Analog control by voltage modulation may require the use of switching components (for example transistors such as MOSFETs) in the control circuitry which generate EMI (however this may be less prevalent when controlling the heater of the conduit due to the lower power requirement of this heater relative to the heater of the humidifier).

Analog control by current modulation may require additional components and control complexity, which may lead to additional cost of components. However, analog control may decrease the need for supply rail capacitors which may reduce the cost of components.

Analog control by resistance modulation may require additional components and control complexity, which may lead to additional cost of components, however due to the lack of switching components in the control circuitry the EMI generated may be lower than other analog control methods.

As shown in FIGS. 4 and 4A, the apparatus 10 comprises conduit heater analog control circuitry 512. The conduit heater analog control circuitry 512 may comprise, for example, a voltage converter (as described in more detail below). The conduit heater analog control circuitry 512 is configured to generate an analog control signal for the conduit heater. In some configurations, the conduit heater analog control circuitry may vary the analog control signal for the conduit heater based on an output from the controller.

In an alternative configuration as shown in FIG. 4A, the apparatus 10 comprises humidifier heater analog control circuitry 514. The humidifier heater analog control circuitry 514 may comprise, for example, a voltage converter (as described in more detail below). The humidifier heater analog control circuitry 514 is configured to generate an analog control signal for the humidifier heater. In some configurations, the humidifier heater analog control circuitry may vary the analog control signal for the humidifier heater based on an output from the controller.

The output from the controller may be a desired duty cycle, power, temperature, therapy parameter level, etc. or a desired change in the parameters thereof.

The controller may compute a necessary analog control signal, or it may only provide a desired power, temperature, therapy parameter level, etc. and the analog control circuitry will adjust the signal accordingly. The analog circuitry may also be configured to receive a desired change from the current signal and/or current power, temperature, therapy parameter level.

As shown in FIGS. 4 and 4A, the apparatus 10 comprises conduit heater digital control circuitry 513. The conduit heater digital control circuitry is configured to generate the pulse-width modulation signal for the conduit heater. In some configurations, the conduit heater digital control circuitry may vary the duty cycle of the pulse-width modulation signal for the conduit heater based on an output from the controller.

The output from the controller may be a desired duty cycle, power, temperature, therapy parameter level, etc. or a desired change in the parameters thereof.

The controller may compute a necessary duty cycle itself, or it may only provide a desired power, temperature, therapy parameter level, etc. and the digital control circuitry will adjust the duty cycle accordingly. The digital control circuitry may also be configured to receive a desired change from the current signal and/or current power, temperature, therapy parameter level.

As shown in FIGS. 4 and 4A, the apparatus 10 comprises humidifier heater digital control circuitry 512. The humidifier heater digital control circuitry 511 is configured to generate the pulse-width modulation signal for the humidifier heater. In the first control scheme, the humidifier heater digital control circuitry 511 is configured to generate the low frequency pulse-width modulation signal, and in the second control scheme, the humidifier heater digital control circuitry 511 is configured to generate the high frequency pulse-width modulation signal.

The digital control circuitry (for example, the conduit heater digital control circuitry 513 and/or the humidifier heater digital control circuitry 511) may comprise one or more switching circuits.

The digital control circuitry (for example, the conduit heater digital control circuitry 513 and/or the humidifier heater digital control circuitry 511) may comprise one or more pulse-width modulation drivers. The pulse-width modulation drivers are configured to generate the pulse-width modulation signal which is provided to the humidifier heater and/or the conduit heater.

The pulse-width modulation drivers may comprise an integrated circuit, a circuit of discrete components, or a mixture of both. For example, the pulse-width modulation drivers can comprise control circuits, MOSFET gate driver circuits, and/or other appropriate PWM hardware as understood in the art.

In some configurations, the humidifier heater digital control circuitry 511 may comprise a pulse-width modulation driver configured to generate the pulse-width modulation signal for the conduit heater.

In some configurations, the humidifier heater digital control circuitry 511 may comprise a pulse-width modulation driver configured to generate the high frequency pulse-width modulation signal and the low frequency pulse-width modulation signal.

When the apparatus is controlling the heater of the conduit according to a second control scheme, the analog control circuitry is disabled.

Disabling the analog control circuitry may comprise switching off a voltage source for the circuit and/or bypassing the circuit, and/or short-circuiting the analog control circuit and/or disconnecting the analog control circuit from the respective heater.

When the apparatus is controlling the heater of the conduit according to a first control scheme, the conduit pulse-width modulation driver circuitry is disabled.

Disabling the conduit pulse-width modulation driver circuitry may comprise switching off a voltage source for the circuit and/or bypassing the circuit, and/or short-circuiting the circuit and/or disconnecting the circuit from the respective heater.

The apparatus may comprise one or more supply rail capacitors. The supply rail capacitors may be located:

a) at an output of the battery b) at an output of the mains power supply c) at one or more of an output of the battery or an output of the mains power supply conversion circuits outputs d) any combination of a)-c).

The frequency of the low frequency pulse-width modulation signal of the first control scheme may be less than about 20 Hz, or about 20 Hz to about 1 KHz.

The frequency of the high frequency pulse-width modulation signal of the second control scheme may be about 25 kHz, or about 1 kHz to about 50 KHz.

The frequency of the high frequency pulse-width modulation signal may be about 1250 times greater than the frequency of the low frequency pulse-width modulation signal.

The frequency of the high frequency pulse-width modulation signal may be about 50 to about times 2000 times greater than the frequency of the low frequency pulse-width modulation signal.

The controller 13 may control the duty cycle of the pulse-width modulation signal (optionally the low frequency pulse-width modulation signal and/or the high frequency pulse-width modulation signal i.e., in the examples as shown in FIGS. 5 and 5B).

The controller 13 may control the duty cycle of the pulse-width modulation signal provided to the heater of the humidifier.

The controller 13 may control the duty cycle of the pulse-width modulation signal provided to the heater of the conduit.

It will be appreciated that the control of the duty cycle of the pulse-width modulation signal may be undertaken in any scheme where digital control is used.

The controller 13 may control the duty cycle of pulse-width modulation signal provided to the heater of the conduit separately to the duty cycle of pulse-width modulation signal provided to the heater of the humidifier.

The controller 13 may control the duty cycle of the pulse-width modulation signal (optionally the low frequency pulse-width modulation signal and/or the high frequency pulse-width modulation signal) provided to the heater of the humidifier and/or to the heater of the conduit according to a humidification control algorithm.

The humidification control algorithm may be that described in U.S. Pat. Nos. 7,306,205 or 8,616,202, both of which are incorporated by reference.

The humidification control algorithm may comprise controlling the apparatus to provide humidity to a therapy humidity level. In some configurations, the apparatus may be configured to control to a dew point as a therapy humidity level.

In some configurations, the controller of the apparatus is configured to determine a desired temperature of the heater of the humidifier (for example a heater plate) based on one or more of a flow sensor, a humidity sensor, and temperature sensor upstream of the humidification chamber.

The desired heater plate temperature may be used to control the power provided to the heater of the humidifier based on the measured heater plate temperature.

In some configurations, the chamber outlet temperature sensor may also be used for closed loop control of the heater plate power.

In some configurations, the controller of the apparatus is configured to determine a desired chamber outlet temperature based on one or more of an ambient temperature sensor, a flow sensor, and optionally a heater of the humidifier temperature sensor and optionally a chamber outlet sensor.

The desired chamber outlet temperature may be used to control the power to the heater plate based on the measured chamber outlet temperature (for example measured by a chamber outlet sensor).

In some configurations, the heater conduit (for example a heater wire) may be controlled based on an end of conduit temperature sensor (for example a patient end temperature sensor). The desired end of conduit temperature may be determined based on the desired humidity (for example the therapy humidity level). In one example the end of conduit temperature is controlled to be at least 3 degrees Celsius above the temperature of the gases exiting the chamber and/or the dew point of the gases exiting the chamber (measured for example by a chamber outlet temperature sensor). The heater of the conduit may be controlled to maintain the temperature of gases above the dew point of gases exiting the chamber.

In some configurations, the controller may be configured to control power to the heater of the humidifier. The controller may control the power provided to the based on at least the ambient temperature sensor, flow sensor, and optionally a heater of the humidifier temperature sensor and further optionally a chamber outlet sensor.

The controller 13 may control the duty cycle of the pulse-width modulation signal (optionally the low frequency pulse-width modulation signal and/or the high frequency pulse-width modulation signal) provided to the heater of the humidifier and/or to the heater of the conduit based on one or more therapy parameters (for example, a therapy humidity level (for example, a relative or absolute humidity, or a dew point)). The controller may control the duty cycle to control the apparatus to one or more therapy parameters.

The duty cycle of the pulse-width modulation signal (optionally the low frequency pulse-width modulation signal and/or the high frequency pulse-width modulation signal) provided to the heater of the humidifier may be based on a desired power of the heater of the humidifier. In some configurations, the desired power may be output by the controller to control the apparatus to one or more therapy parameters as described elsewhere in the specification.

The controller 13 may control the duty cycle of the pulse-width modulation signal provided to the heater of the conduit and/or the heater of the humidifier, based on a desired end of conduit (i.e., patient end) temperature of the flow of gases in the conduit.

The duty cycle of the pulse-width modulation signal (optionally the low frequency pulse-width modulation signal and/or the high frequency pulse-width modulation signal) provided to the heater of the conduit may be based on a desired power of the heater of the conduit. In some configurations, the desired power may be output by the controller to control the apparatus to one or more therapy parameters as described elsewhere in the specification.

The controller is configured to measure the power provided to the heater of the humidifier and control the duty cycle of the pulse-width modulation signal (optionally the low frequency pulse-width modulation signal and/or the high frequency pulse-width modulation signal) based on the measured power provided to the heater of the humidifier and the desired power of the heater of the humidifier.

The controller is configured to measure the power provided to the heater of the conduit and control the duty cycle of the pulse-width modulation signal (optionally the low frequency pulse-width modulation signal and/or the high frequency pulse-width modulation signal) based on the measured power provided to the heater of the conduit and the desired power of the heater of the conduit.

The duty cycle of the pulse-width modulation signal (optionally the low frequency pulse-width modulation signal and/or the high frequency pulse-width modulation signal) may be based on a desired temperature of the heater of the humidifier and/or the heater of the conduit.

The desired power requirement and/or desired temperature may be based on one or more therapy parameters of the apparatus.

The frequency of the pulse-width modulation signal provided to the heater of the conduit by the second control scheme is less than about 20 Hz, or about 20 Hz to about 1 kHz (for example as a low frequency pulse width modulation signal).

As described elsewhere in the specification, the low frequency pulse width modulation signal may be within a frequency range so as to minimize EMI generation, while achieving the desired power output to the heater.

As for, example, described above, controlling the heater of the conduit by analog control may comprise providing an analog control signal (for example a voltage signal) to the heater of the conduit. In some configurations, controlling the heater of the conduit by analog control comprises providing a current to the heater of the conduit.

The controller 13 may control the analog control signal (for example a voltage signal) provided to the heater of the conduit and/or the heater of the humidifier based on one or more therapy parameters (for example, a therapy temperature of the gases provided to the user).

In some configurations, the voltage provided to the heater of the conduit and/or the heater of the humidifier is based on at least in part the resistance of the heater of the conduit.

In some configurations, the heater of the conduit is primarily a resistive load. The heater of the conduit may have minimal parasitic capacitance and inductance.

The analog control signal (for example, a voltage signal) provided to the heater of the conduit may be controlled based on a desired power of the heater of the conduit.

The analog control signal (for example, a voltage signal) provided to the heater of the humidifier may be controlled based on a desired power of the heater of the humidifier.

The controller 13 may be configured to measure the power provided to the heater of the conduit, and analog control signal (for example, the voltage signal) provided to the heater of the conduit is controlled based on the measured power provided to the heater of the conduit and a desired power of the heater of the conduit.

The controller 13 may be configured to measure the power provided to the heater of the humidifier, and analog control signal (for example, the voltage signal) provided to the heater of the humidifier is controlled based on the measured power provided to the heater of the humidifier and a desired power of the heater of the humidifier.

The voltage signal provided to the heater of the conduit and/or the heater of the humidifier may have a quadratic relationship with the input power (for example, the measured power provided to the heater conduit) for example as the heater of the conduit and/or the heater of the humidifier is/are primarily a resistive load.

The analog control signal (for example a voltage signal) provided to the heater of the conduit and/or the heater of the humidifier may be controlled based on a desired end of conduit (i.e., patient end) temperature of the flow of gases in the conduit.

The voltage signal provided to the heater of the conduit and/or the heater of the humidifier may be controlled by one of more voltage converters.

The current signal (in analog control by current modulation) may be provided to the heater of the conduit and/or the heater of the humidifier by a current-mode controlled (CMC) buck converter.

It will be appreciated the current signal (in analog control by current modulation) may be provided to the heater of the conduit and/or the heater of the humidifier by control of one of more voltage converters based on the output of one or more current sensors.

The one or more voltage converters may comprise a DC-DC converter.

The voltage converters may a voltage-mode controlled (VMC) buck converter.

In some configurations, the one or more voltage converters may comprise:

a) A step-down converter
b) A DC-DC converter
c) A step-up converter
d) A boost converter
e) A half bridge converter
f) A flyback converter
g) A push-pull converter
h) A switching converter
i) A switching regulator
j) A linear regulator
k) A linear converter
l) A buck converter
m) A transformer
n) Any combination of a)-m)

The voltage converter may be or may be part of the analog control circuitry.

The invention claimed is:

1. A breathing assistance apparatus comprising:

a humidifier configured to be pneumatically connected to a flow generator and to humidify the flow of gases generated by the flow generator, wherein the humidifier comprises a heater, wherein the apparatus is configured to be connected to a conduit that conveys the flow of gases, wherein the conduit comprises a heater configured to heat the flow of gases within the conduit, a battery, wherein the apparatus is configured to be powered by the battery or a mains power supply, a controller configured to control the heater of the humidifier according to at least a first control scheme and a second control scheme, wherein when the apparatus is powered by the battery the controller is configured to control the heater of the humidifier according to the first control scheme, the first control scheme comprising providing the heater of the humidifier with a high frequency pulse-width modulation signal, and wherein when the apparatus is powered by the mains power supply the controller is configured to control the heater of the humidifier according to the second control scheme, the second control scheme comprising providing the heater of the humidifier with a low frequency pulse-width modulation signal, and wherein the frequency of the high frequency pulse-width modulation signal is greater than the frequency of the low frequency pulse-width modulation signal.

2. The breathing assistance apparatus of claim 1, wherein the heater of the humidifier comprises a heater plate, and the heater plate is configured to heat a fluid in a humidification chamber to humidify the flow of gases.

3. The breathing assistance apparatus of claim 1, wherein the heater of the conduit comprises a heater wire, wherein the heater wire is an electrically conductive heating element.

4. The breathing assistance apparatus of claim 3, wherein the heater wire is at least one of:

in a lumen of the conduit, within a wall of the conduit, embedded in the wall of the conduit, embedded in a bead which forms the breathing conduit or located on an external surface of the conduit.

5. The breathing assistance apparatus of claim 1, wherein the apparatus comprises the flow generator configured to generate the flow of gases.

6. The breathing assistance apparatus of claim 1, wherein the apparatus is configured to detect whether the apparatus is operating on the battery or the mains power supply, wherein the apparatus is configured to operate on the battery when no mains power supply is detected.

7. The breathing assistance apparatus of any one of claim 1, wherein the apparatus is configured to operate on the battery based on an input from a user.

8. The breathing assistance apparatus of claim 1, wherein the battery is located in the apparatus.

9. The breathing assistance apparatus of claim 1, wherein the battery is configured to be connectable and disconnectable from the apparatus.

10. The breathing assistance apparatus of claim 1, wherein the apparatus comprises one or more supply rail capacitors.

11. The breathing assistance apparatus of claim 10, wherein the one or more supply rail capacitors are configured to be located at one or more of:

an output of the battery, an output of the mains power supply, or one or more of an output of a battery conversion circuit and/or an output of a mains power supply conversion circuit.

12. The breathing assistance apparatus of claim 1, wherein the apparatus comprises digital control circuitry configured to generate the high frequency pulse-width modulation signal and/or the low frequency pulse-width modulation signal.

13. The breathing assistance apparatus of claim 12, wherein the digital control circuitry comprises one or more switching circuits.

14. The breathing assistance apparatus of claim 12, wherein the digital control circuity comprises one or more pulse-width modulation drivers.

15. The breathing assistance apparatus of claim 12, wherein the digital control circuity comprises a pulse-width modulation driver for the heater of the humidifier configured to generate the high frequency pulse-width modulation signal and the low frequency pulse-width modulation signal.

16. The breathing assistance apparatus of claim 1, wherein the apparatus comprises a housing, and the flow generator and/or the humidifier are located in the housing.

17. The breathing assistance apparatus of claim 1, wherein the apparatus comprises a gases inlet and a gases outlet, wherein the conduit is configured to be connected to the gases outlet.

18. A breathing assistance apparatus comprising:

a humidifier configured to be pneumatically connected to a flow generator and to humidify the flow of gases generated by the flow generator, wherein the humidifier comprises a heater, a controller configured to control the heater of the humidifier according to at least a first control scheme and a second control scheme, wherein when the apparatus is powered by a first type of power source, the controller is configured to control the heater of the humidifier according to the first control scheme, the first control scheme comprising controlling the heater of the humidifier with a high frequency pulse-width modulation signal, and wherein when the apparatus is powered by a second type of power source, the controller is configured to control the heater of the humidifier according to the second control scheme, the second control scheme comprising providing the heater of the humidifier with a low frequency pulse-width modulation signal, and wherein the frequency of the high frequency pulse-width modulation signal is greater than the frequency of the low frequency pulse-width modulation signal.

* * * * *